United States Patent
Hayashi et al.

(10) Patent No.: US 11,345,762 B2
(45) Date of Patent: May 31, 2022

(54) METHOD FOR PREPARING LIQUID MEDIUM COMPOSITION, AND PREPARATION DEVICE AND KIT THEREFOR

(71) Applicant: NISSAN CHEMICAL INDUSTRIES, LTD., Tokyo (JP)

(72) Inventors: Hisato Hayashi, Funabashi (JP); Koichiro Saruhashi, Funabashi (JP); Tatsuro Kanaki, Shiraoka (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 95 days.

(21) Appl. No.: 15/565,022

(22) PCT Filed: Apr. 7, 2016

(86) PCT No.: PCT/JP2016/061357
§ 371 (c)(1),
(2) Date: Oct. 6, 2017

(87) PCT Pub. No.: WO2016/163444
PCT Pub. Date: Oct. 13, 2016

(65) Prior Publication Data
US 2018/0112013 A1    Apr. 26, 2018

(30) Foreign Application Priority Data
Apr. 7, 2015    (JP) .............................. JP2015-078795

(51) Int. Cl.
*C08B 37/00* (2006.01)
*C12N 5/00* (2006.01)
(Continued)

(52) U.S. Cl.
CPC ........... *C08B 37/006* (2013.01); *A61J 1/2096* (2013.01); *B01J 19/24* (2013.01); *C08J 3/2053* (2013.01);
(Continued)

(58) Field of Classification Search
None
See application file for complete search history.

(56) References Cited

U.S. PATENT DOCUMENTS 4,829,002 A * 5/1989 Pattillo ................. C12M 23/14
435/297.1
2012/0122823 A1 * 5/2012 Reed .................. A61K 47/6951
514/165

(Continued)

FOREIGN PATENT DOCUMENTS

EP    0266058 A2    5/1988
EP    2653494 A1    10/2013
(Continued)

OTHER PUBLICATIONS

Sigma-Aldrich, https://www.sigmaaldrich.com/chemistry/stockroom-reagents/learning-center/technical-library/needle-gauge-chart.html, accessed Oct. 22, 2019.*
(Continued)

*Primary Examiner* — Erin M. Bowers
(74) *Attorney, Agent, or Firm* — Leydig, Voit & Mayer, Ltd.

(57) ABSTRACT

The present invention provides a method capable of easily mixing any liquid containing a linking substance such as a divalent metal cation and the like with a liquid containing a particular compound at a high concentration, and capable of producing a liquid medium composition comprising fine structures dispersed therein, and a production device therefor and a kit therefor. The first liquid containing a particular
(Continued)

compound is passed through a through-hole having a given cross-sectional area formed in a nozzle part at a given flow rate and injected into the second liquid at a given flow rate. By this simple operation, a structure in which the particular compound is bonded via the linking substance is formed, and the structure is preferably dispersed in a mixture of the both liquids.

10 Claims, 7 Drawing Sheets

(51) Int. Cl.
  *A61J 1/20* (2006.01)
  *B01J 19/24* (2006.01)
  *C08J 3/205* (2006.01)
(52) U.S. Cl.
  CPC ......... *C12N 5/0068* (2013.01); *B01J 2219/24* (2013.01); *C08J 2305/00* (2013.01)

(56) References Cited

U.S. PATENT DOCUMENTS

| | | | |
|---|---|---|---|
| 2013/0130382 A1 | 5/2013 | Honmou et al. | |
| 2014/0106348 A1* | 4/2014 | Nishino | G01N 33/5044 435/6.11 |

FOREIGN PATENT DOCUMENTS

| | | | |
|---|---|---|---|
| EP | 2878664 A1 | | 6/2015 |
| JP | S59-141420 A | | 8/1984 |
| JP | H05-277156 A | | 10/1993 |
| JP | 2009-045140 | * | 3/2009 |
| JP | 2009-045140 A | | 3/2009 |
| JP | 2011-152353 A | | 8/2011 |
| JP | 2011-212361 A | | 10/2011 |
| WO | WO 1998/057734 A1 | | 12/1998 |
| WO | WO 98/57734 | * | 7/2008 |
| WO | WO 2012/018040 A1 | | 2/2012 |
| WO | WO 2014/017513 A1 | | 1/2014 |

OTHER PUBLICATIONS

Smith et al., J. Biomaterials Applications 22(3): 241-254 (2007).*
Kelcogel Gellan Gum Book, 5th Edition, Jul. 2008.*
Hossain et al., "Development of microspheres for biomedical applications: a review," *Prog. Biomater.*, 4(1): 1-19 (2015).
Lee et al., "Size and Shape of Calcium Alginate Beads Produced by Extrusion Dripping," *Chem. Eng. Technol.*, 36(10): 1627-1642 (2013).
Poncelet et al., "Theory of electrostatic dispersion of polymer solutions in the production of microgel beads containing biocatalyst," *Adv. Colloid Interface Sci.*, 79(2-3): 213-228 (1999).
Japanese Patent Office, International Search Report in International Patent Application No. PCT/JP2016/061357 (dated Jul. 12, 2016).
Jen et al., "Review: Hydrogels for Cell Immobilization," *Biotechnol. Bioeng.*, 50(4): 357-364 (1996).
China National Intellectual Property Administration, Office Action in Chinese Patent Application No. 201680021238.X (dated Mar. 9, 2020).

* cited by examiner (a)

(b)

(c)

(a)

(b)

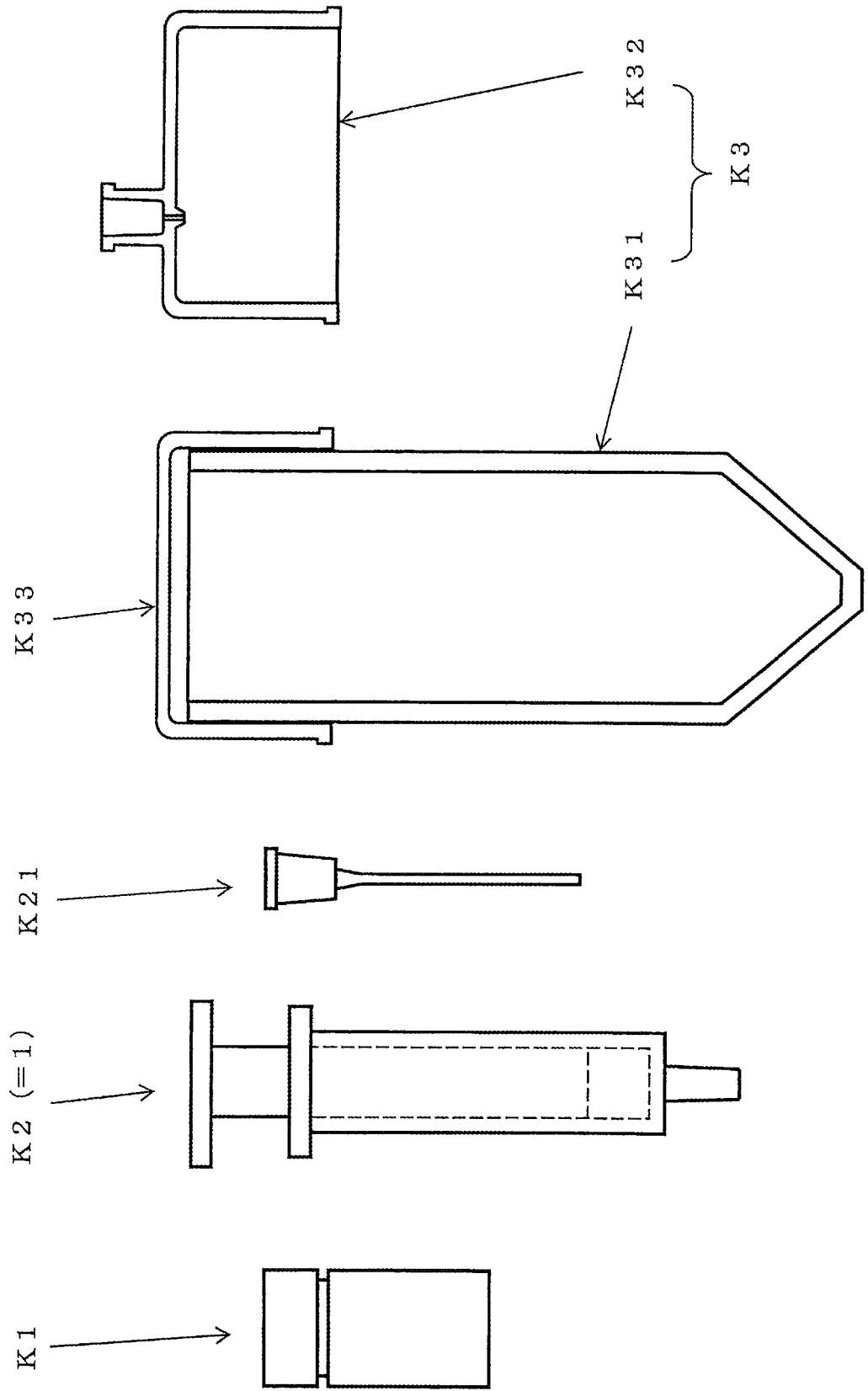

METHOD FOR PREPARING LIQUID MEDIUM COMPOSITION, AND PREPARATION DEVICE AND KIT THEREFOR

CROSS-REFERENCE TO RELATED APPLICATIONS

This patent application is the U.S. national phase of International Patent Application No. PCT/JP2016/061357, filed on Apr. 7, 2016, which claims the benefit of Japanese Patent Application No. 2015-078795, filed on Apr. 7, 2015, the disclosures of which are incorporated herein by reference in their entireties for all purposes.

TECHNICAL FIELD

The present invention relates to a production method of a liquid medium composition, and a production device and a kit for carrying out the method. More particularly, the present invention relates to a production method including appropriately mixing at least two kinds of liquids to be mixed for forming the above-mentioned medium composition (the first liquid containing a particular compound, and the second liquid containing a substance for linking the particular compounds to form a structure) to produce a liquid medium composition comprising the above-mentioned structure dispersed therein, a production device and a kit enabling the dispersing thereof.

Background Art

In recent years, techniques for proliferating or maintaining in vitro various organs, tissues and cells that play distinct roles in the body of animals and plants have been developed. Proliferation or maintenance of the organs and tissues in vitro is called organ culture and tissue culture, respectively, and proliferating, differentiating or maintaining in vitro the cells separated from an organ or tissue is called cell culture.

Cell culture is a technique for proliferating, differentiating or maintaining separated cells in vitro in a medium, and is indispensable for detailed analyses of the in vivo function and structure of various organs, tissues and cells.

In addition, the cells and/or tissues cultured by the technique are utilized in various fields including efficacy and toxicity evaluation of chemical substances, pharmaceutical products and the like, large-scale production of useful substances such as enzymes, cell growth factors, antibodies and the like, regenerative medicine supplementing organ, tissue and cells that were lost by disease and deficiency, improvement of plant brand, production of gene recombinant products, and the like.

As a medium for culturing cells and the like (organ, tissue, cells), a liquid medium can be mentioned, and the present inventors successfully developed a liquid medium composition enabling culture of cells and the like in a suspending state (patent documents 1 and 2).

The liquid medium composition described in patent document 1 is one in which particular compounds (particularly, a polymer compound having an anionic functional group) assemble via a divalent metal cation and the like to form amorphous structures, and the structures are dispersed in a liquid medium in a suspended state. In the following, the above-mentioned particular compound such as a polymer compound having an anionic functional group and the like is also referred to as a "particular compound", and a substance such as a divalent metal cation and the like which binds the particular compounds is also referred to as a "linking substance".

The medium composition provides a preferable liquid medium capable of culturing cells and the like in a suspended state without accompanying an operation such as shaking, rotation and the like having a risk of causing damage and loss of functions of cells and the like.

DOCUMENT LIST

Patent Documents patent document 1: WO 2014/017513
patent document 2: US 2014/0106348 A1

SUMMARY OF THE INVENTION

Problems to be Solved by the Invention

The originally-intended preferable state of the liquid medium composition described in the above-mentioned patent document 1 is a state in which small amounts of the particular compounds are linked to each other to form fine structures and many structures are dispersed in a liquid.

However, the present inventors studied the actual production steps of the liquid medium composition in detail, and found that to achieve such preferable state, it is necessary to ensure that the structure is not unevenly formed locally in the medium composition. For example, when the particular compound is deacylated gellan gum, it forms an indeterminate amorphous structure via a linking substance ((e.g., calcium ion) in a liquid medium when mixed with the liquid medium, and the structure becomes a carrier for suspending cells and the like. However, in a mixing method including pouring a liquid containing a particular compound at a high concentration into a liquid medium containing a linking substance while stirring the medium, the particular compound contacts with the linking substance at the moment the both liquids flow together to form the structure. As a result, the structures are sometimes linked to form a long string suspended in the mixture (or string structure entangled in a mass), which is not the originally-intended dispersed state. It was also found that such state is developed even when the mixture is stirred at a comparatively high speed. Once such string structure is formed in the liquid medium, it is not easy to cleave the structure finely and disperse same in the base material in view of the property of the structure that a double helix formed by the molecular chain forms a tight 3-dimensional network with each other via a linking substance (e.g., calcium ion).

To afford a state of the structure finely dispersed in the liquid medium, a special treatment for dispersing may be performed, which includes, for example, using a powder medium or a liquid medium of known components such as concentrated medium and the like, diluting a liquid containing a particular compound, and mixing them to produce a state of dispersion of fine structures.

However, such special treatment for dispersing takes time and effort and is sometimes difficult to perform on conventional liquid medium and special liquid medium, which in turn limits the cells and the like to be cultured.

An object of the present invention is to solve the above-mentioned problem, and provides a method capable of easily mixing any liquid containing a linking substance such as a divalent metal cation and the like with a liquid containing a particular compound at a high concentration, and capable of producing a liquid medium composition comprising fine structures dispersed therein, and a production device therefor and a kit therefor.

Means of Solving the Problems

The present inventors have conducted intensive studies and found that a liquid medium composition comprising a liquid medium and fine structures preferably dispersed in the liquid medium can be obtained without using a special stirring apparatus and by passing a liquid containing a particular compound through a through-hole having a cross section in a particular range at a flow rate not less than a particular value, and merely injecting the liquid at said flow rate into a liquid containing a linking substance, which resulted in the completion of the present invention.

The main constitution of the present invention is as follows.

[1] A production method of liquid medium composition, comprising steps of:

passing a first liquid comprising a particular compound of the following (i) through a through-hole having a cross-sectional area of 0.01 mm$^2$-5.00 mm$^2$ formed in a nozzle part at a flow rate of not less than 1.7 mL/sec, injecting the first liquid into a second liquid comprising a linking substance of the following (ii) at said flow rate to form structures in which the particular compounds are bound via the linking substance and disperse the structures in a mixture of the both liquids mentioned above:

(i) a particular compound which is a polymer compound having an anionic functional group, and capable of forming a structure by linking via a divalent metal cation, which structure being capable of suspending a cell or a tissue, (ii) a linking substance which is a divalent metal cation.

[2] The production method of the above-mentioned [1], wherein the second liquid is placed in a container of the following (a), the first liquid is fed out from a supply device and passed through the through-hole of a container of the following (a) at the above-mentioned flow rate, whereby the first liquid is injected into the second liquid in the container at the above-mentioned flow rate:

(a) a container comprising a body and a lid, said body or lid provided with a nozzle part having a through-hole communicating the outside of the container and the inside of the container, and said through-hole having a cross-sectional area of 0.01 mm$^2$-5.00 mm$^2$.

[3] The production method of the above-mentioned [2], wherein the supply device is a syringe, and the nozzle part is provided on the lid of the container, and a tubular component for fitting a syringe tip protrudes from an outer surface of the lid at a container external side of the nozzle part.

[4] The production method of the above-mentioned [1], wherein the second liquid is placed in a container of the following (a), a tip of a nozzle part of a supply device of the following (b) containing the first liquid is inserted into the container, the first liquid is fed out from the supply device and passed through the through-hole in the nozzle part of the supply device, whereby the first liquid is injected into the second liquid in the container at the above-mentioned flow rate:

(b) a supply device comprising a container part for containing a liquid, and a nozzle part for injecting the contained liquid through a through-hole, said through-hole having a cross-sectional area of 0.01 mm$^2$-5.00 mm$^2$.

[5] The production method of the above-mentioned [4], wherein the supply device is a syringe, and the nozzle part is an injection needle mounted on the syringe, the lid of the container is provided with a penetrable part permitting penetration of a needle tube part of the injection needle from the outside of the container to the inside of the container, and a tubular component for fitting a needle base part of the injection needle protrudes from an outer surface of the lid at a container external side of the penetrable part.

[6] The production method of any one of the above-mentioned [1] to [5], wherein the particular compound of (i) is deacylated gellan gum, the first liquid is an aqueous solution containing deacylated gellan gum, the linking substance of (ii) is one or both of calcium ion and magnesium ion, and the second liquid is a liquid medium containing one or both of calcium ion and magnesium ion.

[7] A production device for carrying out the production method of the above-mentioned [1], comprising a supply device for feeding out the first liquid, a container for containing the second liquid and receiving the first liquid fed out from the supply device, and a nozzle part having a through-hole through which the first liquid passes when fed out from the supply device into the container, wherein the through-hole has a cross-sectional area of 0.01 mm$^2$-5.00 mm$^2$, and the supply device is configured to feed out the first liquid at the flow rate of not less than 1.7 mL/sec, which is configured to be able to inject the first liquid into the container at a flow rate of not less than 1.7 mL/sec by passing the first liquid through the through-hole at the above-mentioned flow rate.

[8] The production device of the above-mentioned [7], wherein the nozzle part having the through-hole is provided as a part of the container, and the container has a body and a lid, and the nozzle part is provided in the body or lid of the container such that the through-hole communicates the outside of the container and the inside of the container.

[9] The production device of the above-mentioned [8], wherein the supply device is a syringe, the nozzle part is provided on the lid of the container, and a tubular component for fitting a syringe tip protrudes from an outer surface of the lid at a container external side of the nozzle part.

[10] The production device of the above-mentioned [7], wherein the supply device is a syringe, the nozzle part is an injection needle mounted on the syringe, the lid of the container is provided with a penetrable part permitting penetration of the injection needle from the outside of the container to the inside of the container, and a tubular component for fitting a needle base part of the injection needle further protrudes from an outer surface of the lid at a container external side of the penetrable part.

[11] A kit for carrying out the production method of the above-mentioned [1], comprising at least a first container, a syringe, and a second container, wherein the first container contains the first liquid of the above-mentioned [1], the syringe is the syringe of the above-mentioned [3] functioning as a supply device for feeding out the first liquid, the second container is the container (a) of the above-mentioned [2] for containing the second liquid of the above-mentioned [1] and, as described in the above-mentioned [3], the nozzle part is provided on the lid of the container, and a tubular component for fitting a syringe tip protrudes from an outer surface of the lid at a container external side of the nozzle part.

[12] The kit of the above-mentioned [11], wherein the second container is further equipped with a sealing lid free of a nozzle part and configured to be able to seal the inside of the body of the container, and the lid of the container (a) of the above-mentioned [2] and the above-mentioned sealing lid can be compatibly mounted on an opening part of the body of the container.

[13] The kit of the above-mentioned [11] or [12], wherein the above-mentioned syringe is further equipped with a tubular component to be inserted in the first container and used to suck the first liquid, said tubular component comprising a thin-tube part having an outer diameter permitting insertion into the first container, and a length enabling suction of the first liquid from the first container, and a connecting part at one end of the thin-tube part, mountable on the tip of the cylinder of the syringe.

Effect of the Invention

As described in the explanation of the above-mentioned Background Art, in a general stirring and mixing method including pouring a liquid (first liquid) containing a particular compound at a high concentration into a liquid medium (second liquid) containing a linking substance while stirring the medium, the structures are sometimes linked to form a long string suspended in the mixture. The reason is that even if a stirring bar is rotated at a high speed in the liquid medium, only the stirring bar moves certainly at a high speed, and the entire second liquid (in particular, around liquid surface where the first liquid is poured into) does not move as fast as the stirring bar.

To improve this, for example, a constitution in which the stirring bar is moved closer to the junction where the first liquid is poured into and stirs the mixture while cutting the junction is considered. Such constitution requires a special stirring apparatus which can be operated in a sterile or sealed state to avoid biological contamination. When individual production of a medium composition in a large number of small capacity containers is desired and the like, an open system is created when a stirrer is inserted into the container, and therefore, a special facility to secure sterile condition such as clean room, clean booth and the like needs to be installed. From such aspect, individual use of such special stirring apparatus for each small capacity container is difficult.

In contrast, the principle of the mixing method of the both liquids in the production method and production device of the present invention is completely opposite to the principle of the above-mentioned conventional mixing methods, and the second liquid is not stirred at a high speed but the first liquid is injected at a flow rate Q (or flow velocity V) not less than a given value by passing the liquid through a through-hole having a predetermined cross-sectional area S so that the first liquid is injected into the second liquid at the flow rate Q (or flow velocity V). In this way, the difference in the speed of the both liquids at the junction where the both liquids meet can be certainly increased, whereby the both liquids contact with impact and long string of the structures can be sufficiently suppressed. Once fine structures are formed, even when the fine structures gather in one part of the mixture, they can be homogeneously dispersed throughout the whole mixture in a container by further stirring.

In the present invention, the cross-sectional area S of the through-hole in the nozzle part is limited to 0.01 mm$^2$-5.00 mm$^2$ to set the first liquid to a flow rate of not less than 1.7 mL/sec (L is liter). The cross section of the through-hole is a section of the through-hole when it is cut perpendicularly to the central axis from the inlet opening to the outlet opening of the through-hole, and the cross-sectional area of the through-hole is an area of the cross-section of the through-hole.

The flow rate Q of the first liquid that passes through the outlet opening of the through-hole, the cross-sectional area S of the through-hole, and the flow velocity V of the first liquid that passes through the outlet opening of the through-hole show a relationship of $Q=S \times V$.

First, when a through-hole having a large diameter exceeding the above-mentioned cross-sectional area is used, the first liquid forming a thick flow rushes into the second liquid. In such a thick flow, the first liquid in the center part thereof may not be able to contact the second liquid before stalling. In contrast, when the cross-sectional area of the through-hole is within the above-mentioned range, the injection flow maintains a thin flow, and the first liquid in the center part thereof highly probably contacts the second liquid before stalling. Therefore, in the present invention, the cross-sectional area of the through-hole is limited to the above-mentioned range.

In the cultivation site of cell and the like, a supply device preferable for practical use for feeding out the first liquid is a manual syringe as mentioned below. Therefore, feeding out at a flow rate capable of achieving the preferable flow velocity cannot be certainly performed with ease with a through-hole having a large diameter beyond the above-mentioned cross-sectional area.

In the present invention, therefore, a through-hole having a cross-sectional area in the above-mentioned range is always used even when a large amount of medium composition is produced at once in a container with large capacity. Where necessary, a plurality of through-hole may be used to inject parallelly the first liquid in the second liquid, or a single through-hole may be used to inject the first liquid in the second liquid plural times. The supply device in this case may be one according to the discharge capability thereof, or supply devices may be provided in parallel in the number of the through-holes.

BRIEF DESCRIPTION OF THE DRAWINGS

FIG. 4(a) is a top view of the nozzle part, FIG. 4(b) is a partially-enlarged sectional view of the nozzle part in FIG. 2, FIG. 3, and FIG. 4(c) is a side view of the upper part alone of FIG. 4(b), which is seen from the X direction of the Figure.

FIG. 5(a) is a top view of the lid, and FIG. 5(b) is a side view of the lid and is a sectional view when the lid is cut along line Y-Y in FIG. 5(a).

FIG. 7 is a schematic showing one embodiment of the constitution of the kit of the present invention. In this Figure, the container and the lid are shown in sectional drawings. An appearance of the syringe 1 as a supply device rather than a section thereof is shown.

DESCRIPTION OF EMBODIMENTS

In the following, the production method of the present invention is explained while explaining the constitution of the production device of the present invention. The explanation of the specific constitution of the production device of the present invention is also an explanation of how to practice the production method of the present invention concretely. The description of the production method of the present invention is also an explanation of the method of using the production device of the present invention.

Figure 1:
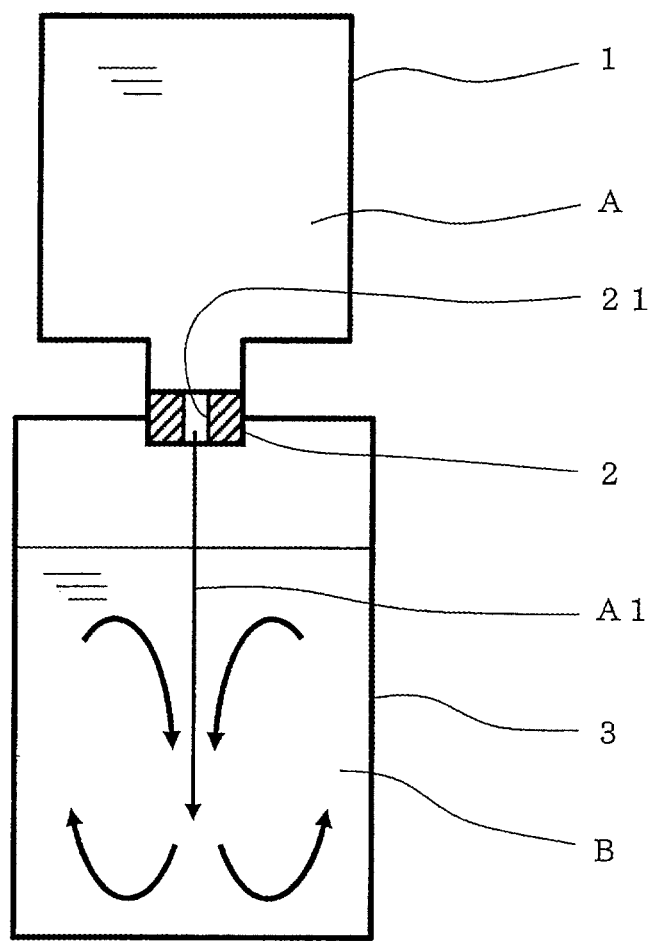
FIG. 1 is a sectional drawing explaining the outline of the production method and the constitution of the production device of the present invention. To divide and stress the regions, the section of the nozzle part is hatched. The constituent elements shown by the symbols in FIG. 1 are: A; the first liquid, B; the second liquid, A1; flow of injected first liquid, 1; supply device, 2; nozzle part, 21; through-hole, 3; container.

The production method of the present invention is preferably a method of preferably producing a liquid medium composition as described in the above-mentioned patent document 1, and includes, as shown in FIG. 1, steps of passing a first liquid A comprising a particular compound of the following (i) through a through-hole 21 having a cross-sectional area S of 0.01 mm$^2$-5.00 mm$^2$ formed in a nozzle part 2 at a flow rate Q of not less than 1.7 mL/sec, and injecting the first liquid with the above-mentioned flow rate Q into a second liquid B comprising a linking substance of the following (ii) to mix the both liquids.

Here, the particular compound of the above-mentioned (i) is a polymer compound having an anionic functional group, and capable of forming a structure by linking via a divalent metal cation, the structure being capable of suspending a cell or a tissue.

The linking substance of the above-mentioned (ii) is a divalent metal cation.

The particular compound, linking substance, and the first and second liquids containing each are described in detail below.

By injecting at the above-mentioned flow rate Q, a liquid medium composition containing a structure having a particular compound bonded via a linking substance formed in a mixture of the above-mentioned both liquids A, B but finely dispersed in the mixture can be obtained.

The flow rate Q of the first liquid A only needs to be not less than 1.7 mL/sec. When the flow rate Q is larger relative to the through-hole having the cross-sectional area S in the above-mentioned range, the first liquid violently rushes into the second liquid and suppresses a long string of the structure.

While the upper limit of the flow rate is not particularly limited, from the aspect of the feed-out capability of the first liquid through-hole in consideration of the cross-sectional area S, it is about 10 mL/sec, more suitably about 5 mL/sec for the actual operation.

The cross-sectional area S of the through-hole 21 in the nozzle part may be 0.01 mm$^2$-5.00 mm$^2$, more preferably 0.05 mm$^2$-2.00 mm$^2$, particularly preferably 0.10 mm$^2$-0.70 mm$^2$. By limiting the cross-sectional area of the through-hole to fall within the above-mentioned range, preferable stirring results (namely, preferable dispersion results of the structures) are obtained even when the amount of the first liquid to be fed out from the supply device may vary somewhat.

The flow direction of the first liquid when it is injected into the second liquid is not particularly limited. As shown in FIG. 1, it may be injected downwardly from the above, or may be lateral injection from the side, or upward injection from the below.

The production device of the present invention is a device configured to carry out the production method of the present invention. As shown in FIG. 1, it is configured to have at least a supply device 1 and a container 3 in addition to the nozzle part 2 having the above-mentioned through-hole 21.

The above-mentioned supply device 1 is a device for feeding out the first liquid A, and configured to feed out the first liquid at the above-mentioned flow rate Q (mm$^3$/sec).

The container 3 is a container for containing the second liquid B and receiving the first liquid fed out from the supply device 1, and forms a mixture of the both liquids (i.e., liquid medium composition to be produced).

The nozzle part 2 has a through-hole 21 having the above-mentioned cross-sectional area (mm$^2$) through which the first liquid passes when it is fed out from the supply device into the container. The nozzle part 2 may be a part belonging to the supply device 1, or a part belonging to the body or lid of the container, or an independent coupling member interlying between the supply device and the container and not belonging to any member.

When the production device is used, the first liquid A is fed out at the above-mentioned flow rate Q (mm$^3$/sec) from the supply device 1, passes through a through-hole 21 having the above-mentioned cross-sectional area S (mm$^2$) and formed in the nozzle part 2, and rushes into the second liquid contained in the container 3. This series of operations carry out the production method of the present invention, whereby a preferable liquid medium composition is obtained as mentioned above.

The volume ratio of the first liquid and the second liquid to be mixed is not particularly limited, and generally, (first liquid:second liquid)=about (1:1)-(1:1000), preferably about (1:5)-(1:500), more preferably about (1:10)-(1:100).

In an actual cultivation operation of cells and the like, to prepare a fresh medium composition when in use, it is sometimes more preferable to individually produce a medium composition in each container having a small capacity of about 1-1000 mL, preferably about 10-200 mL, rather than producing a large amount of the medium composition at once in a single large capacity container and dividing same in each small capacity container for stock.

When a medium composition is individually produced in each container having a small capacity mentioned above, specific capacity of the both liquids to be mixed is preferably about 1 mL-1000 mL, more preferably about 10 mL-200 mL, of the second liquid to be placed in a container, into which about 0.01 mL-100 mL, more preferably about 0.1 mL-20 mL, of the first liquid is injected.

The supply device 1 and the capacity of the container 3 can be appropriately selected according to such combination.

The mixture of the first liquid and the second liquid may be a medium composition as the production object, or may be further added with an additive to produce a medium composition as the production object.

Conversely to the present invention, a medium composition as the production object can also be obtained by placing a small amount of the first liquid in a container and injecting a large amount of the second liquid thereinto. However, since the first liquid is not easily admixed due to high viscosity thereof, the amount of the liquid splashed and scattered on the wall surface and the like relative to the total amount of the liquid is non-negligible and the like, the contact state and dilution conditions are vastly different from those when a small amount of a liquid is injected at a high flow velocity into a large amount of a liquid. In addition, problems occur such as the time required for injection, increase of pressure in the container, and the like. Therefore, in the present invention, injection of the first liquid into the second liquid at the above-mentioned ratio is recommended.

The supply device may be any as long as it has discharge capability permitting feeding out of the first liquid at the above-mentioned flow rate Q (not less than 1.7 mL/sec) and, for example, peristaltic pump, diaphragm pump, syringe and the like can be mentioned. A driving source of the supply device may be manual or may use a drive apparatus such as motor and the like. Among others, a syringe shown in FIG. 2, FIG. 3, FIG. 6 (injection syringe) is a preferable supply device, since it has a simple constitution, is easily handled, is low costly (and therefore, may be disposable), and can achieve the flow rate even by manual pushing. For example, plastic disposable syringe such as Terumo syringe for prophylactic inoculation manufactured by Terumo (1 mL, model number SS-01P)—Terumo syringe manufactured by Terumo (50 mL, model number SS-50ESZ) and the like is suitable for producing a medium composition for each container mentioned above having a small capacity.

The "syringe" in the present invention is a device configured to have a cylinder and a plunger (pusher). The present invention includes an embodiment using a syringe as it is and an embodiment further having an injection needle mounted on a syringe tip.

The upper limit of the flow rate Q when the first liquid is fed out (volume that passes through a certain cross section in the flow per unit time: $mm^3/sec$) is not particularly limited. Since a higher flow rate causes higher flow velocity on passage through a through-hole in the above-mentioned nozzle part, and the first liquid rushes into the second liquid with impact, the structure can be more preferably subdivided and dispersed.

Figure 2:
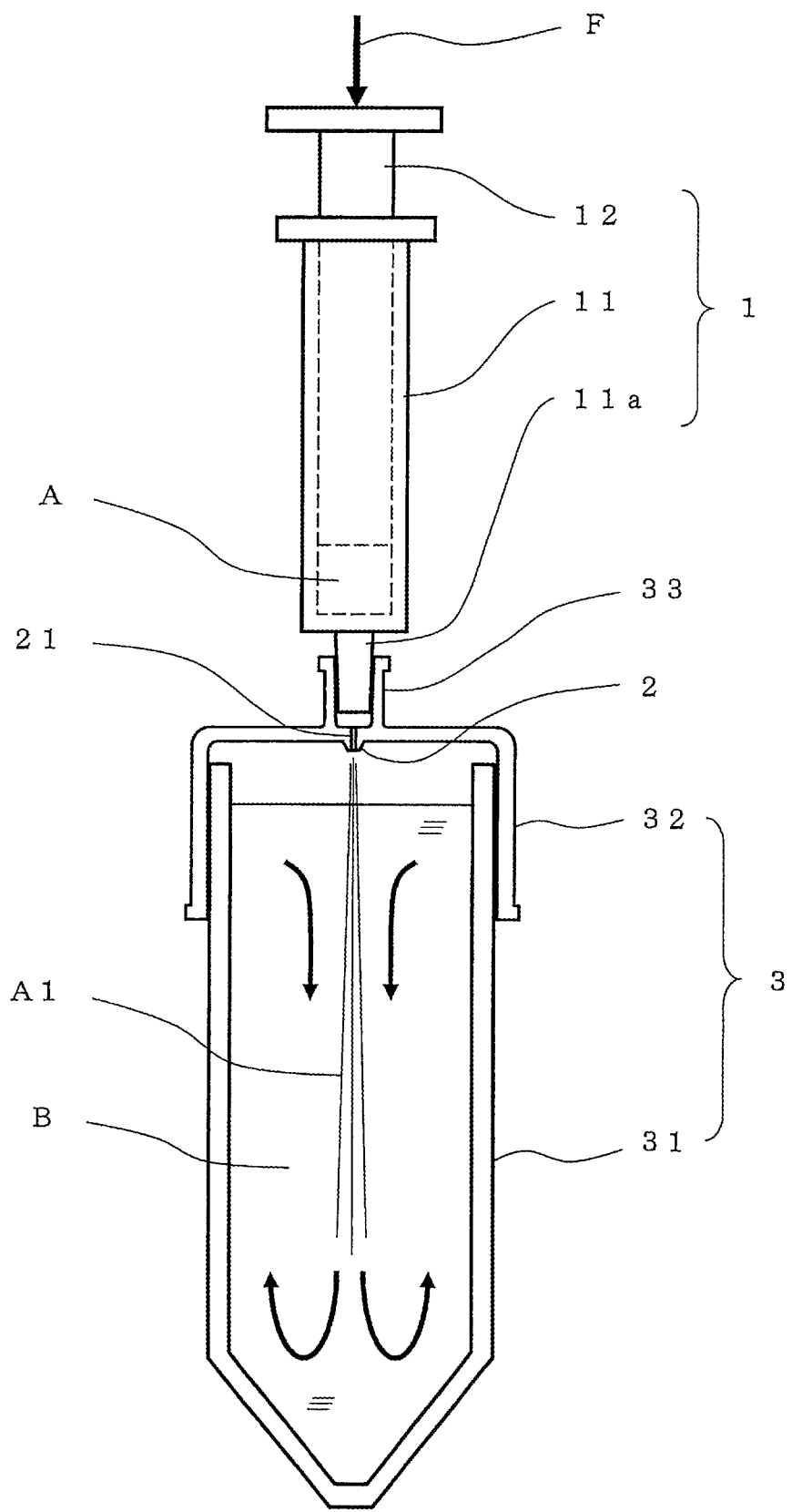
FIG. 2 is a sectional drawing showing a specific embodiment of the production method and the production device of the present invention. In the embodiment of this drawing, the nozzle part belongs to the container side, and the first liquid is configured to be injected in the center of the container. In this Figure, the sections of the body and the lid are shown as end surface drawings of the container, and the appearance of the syringe 1 as a supply device, rather than a section thereof, is shown (same in FIG. 3, FIG. 6). Hatching of the section is omitted (same in FIG. 3-FIG. 7).

When a syringe is used as a supply device, as shown in FIG. 2, a plunger (piston part) 12 is pushed down with a pressing force (load) F capable of achieving the above-mentioned flow rate or flow velocity by passing the first liquid A through a through-hole 21, and the first liquid A contained in a cylinder 11 is fed out.

That is, "passing a first liquid through a through-hole having a cross-sectional area of $0.01\ mm^2$-$5.00\ mm^2$ formed in a nozzle part to achieve a flow rate of not less than 1.7 mL/sec" in the present invention means that pressing force F is applied on the first liquid through a supply device 1 so that the first liquid can pass through a through-hole with the cross-sectional area at a flow rate of not less than 1.7 mL/sec, and the first liquid is extruded by the pressing force through the through-hole at the discharge flow rate.

When a syringe is used as a supply device, the flow rate of the first liquid fed out from the syringe can be adjusting the time required for the whole stroke of the plunger. That is, a syringe is preferable since the flow rate ($mm^3/sec$) of the object can be adjusted by controlling the time necessary for the stroke of the plunger even when it is pushed by human power.

While the upper limit of the flow rate obtained by pushing the syringe by human power varies depending on the power of individual, it is generally about 5 mL/sec.

In an embodiment where a syringe with a small capacity is used, feeding out at a flow rate of not less than 1.7 mL/sec can be achieved when the cross-sectional area of the through-hole is $0.2\ mm^2$, syringe is Terumo syringe for prophylactic inoculation manufactured by Terumo (1 mL, model number SS-01P), 1.7 mL of the first liquid is contained in the syringe, and whole moving (travelling) time T1 of plunger, which is required to extrude the whole first liquid, is not more than 1 second. When the syringe is manually operated and in consideration of the force for pushing the plunger, the whole moving time T1 of the plunger is suitably about 0.2 second-1 second, and the flow rate obtained in this case is 1.7 mL/sec-8.5 mL/sec.

In an embodiment where a syringe with a large capacity is used, feeding out at a flow rate of not less than 1.7 mL/sec can be achieved when the cross-sectional area of the through-hole is $0.2\ mm^2$ which is same as above, syringe is Terumo syringe manufactured by Terumo (50 mL, model number SS-50ESZ), 20 mL of the first liquid is contained in the syringe, the through-hole has the same bore diameter, and whole moving (travelling) time T2 of plunger, which is required to extrude the whole first liquid, is not more than 12 seconds. When the syringe is manually operated and in consideration of the force for pushing the plunger, the whole moving time T2 of the plunger is suitably about 2.5 seconds-12 seconds, and the flow rate obtained in this case is 1.7 mL/sec-8.0 mL/sec. The pressing force (load) necessary in this case is the same as when the above-mentioned small capacity syringe is used.

When the plunger is pushed by human power, it is difficult to maintain the moving speed of the plunger strictly constant. However, when the moving time is within the above-mentioned range, the plunger can be moved without deviating from the range even by human power, whereby the object flow rate and the flow velocity at the outlet opening of the through-hole can be achieved without a large error.

The through-hole in the nozzle part may be any as long as it has a cross-sectional area S in the above-mentioned range and affords a flow rate in the above-mentioned range. While the through-hole preferably has a straight pipe shape, it may have a draft angle for resin molding. The flow A1 of the first liquid when fed out from the through-hole is preferably a linear flow maintaining the cross-section of the through-hole to the possible extent rather than a spreading spray, which in turn enables strong and deep injection into the second liquid. The shape of the through-hole can be appropriately designed to achieve such flow.

The shape of the cross section of the through-hole is not particularly limited, and may be a circular shape, an ellipse shape, an oval shape, a rectangle shape, an oblong shape, an irregular shape or the like. Since formation of the through-hole is easy, the shape of the cross section of the through-hole is preferably a circular shape. To intentionally disturb and diffuse the flow of the injected first liquid, moreover, the shape of the cross section of the through-hole may be appropriately deformed.

The length of the through-hole is not particularly limited. When a nozzle part is set on a container (body or lid), the length of the through-hole is preferably about 0.01 mm-10 mm. When the nozzle part is an injection needle of a syringe, the length of the through-hole is preferably about 1.0 mm-100 mm.

The nozzle part 2 may be positioned at the center of the opening of the container and the like, so that the first liquid A can be injected into the center of the container 3 as shown in FIG. 2. When the first liquid is injected from the nozzle part into the center of the container, an effect of moving around at the bottom of the container as diverged flows can be obtained after the first liquid is deeply injected into the second liquid, as shown with arrows in the container in FIG. 2.

Figure 3:
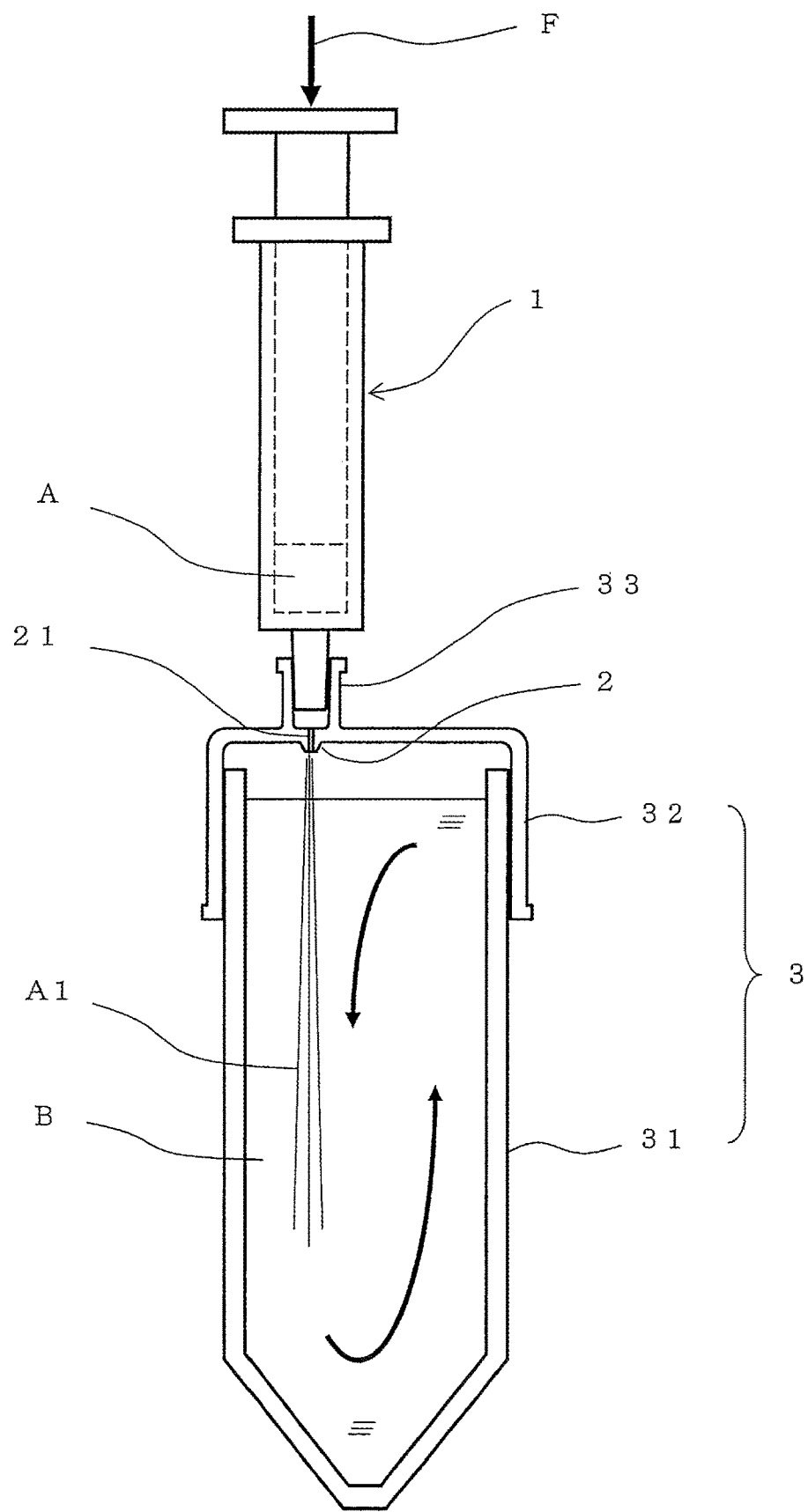
FIG. 3 is a drawing showing other specific embodiment of the production method and the production device of the present invention. In the embodiment of this drawing, the nozzle part belongs to the container side, and the first liquid is configured to be injected in a position eccentric from the center of the container.

Alternatively, the nozzle part 2 may be positioned at a position offset (decentered) from the center of the opening of the container, so that the first liquid can be injected into a position offset from the center toward the periphery of the container, as shown in FIG. 3. When the first liquid is injected into a position offset from the center toward the periphery of the container, the first liquid enters deeply into the second liquid, makes a large turn at the bottom of the container, and affords an effect of moving around as one flow in the container, as shown with arrows in the container in FIG. 3.

The position of the nozzle part can be appropriately determined according to, for example, the viscosity of the first and second liquids, the amount of liquid, the shape of the container and the like.

The container only needs to be able to contain the above-mentioned second liquid, receive injection of the first liquid and can contain a mixture of these. When the first liquid is injected in an airtight state into a container containing the second liquid, the pressure in the container increases. However, when the mixing ratio is about the above-mentioned specific mixing ratio, an increase in the pressure does not pose a particular problem.

The capacity of the container is not particularly limited. A preferable capacity is, for example, about 5 mL-1000 mL from the aspect of the above-mentioned specific mixing ratio. While the cross sectional shape of the container is not particularly limited, a circular shape is preferable for achieving a smooth circulation due to convection during mixing.

The ratio (L1/D1) of depth L1 of the inside of the container and bore diameter D1 is not particularly limited. Even when containers have the same capacity, when the ratio (L1/D1) is excessively high, the container becomes excessive long as a whole and is not preferable since convection during mixing is prevented. When the ratio (L1/D1) is excessively small, the container becomes a thin plate as a whole and is not preferable since convection during mixing is prevented. A preferable ratio (L1/D1) is appropriately determined from about 0.5-30, preferably about 1.0-15, further preferably 2.0-8.0.

When the second liquid is contained in a container, a ratio of depth Z of the part occupied by the liquid (immersion part) and the bore diameter d (Z/d) is not particularly limited, either, and is appropriately determined from about 0.5-20, preferably about 1.0-10, further preferably about 1.3-4.0.

Figure 6:
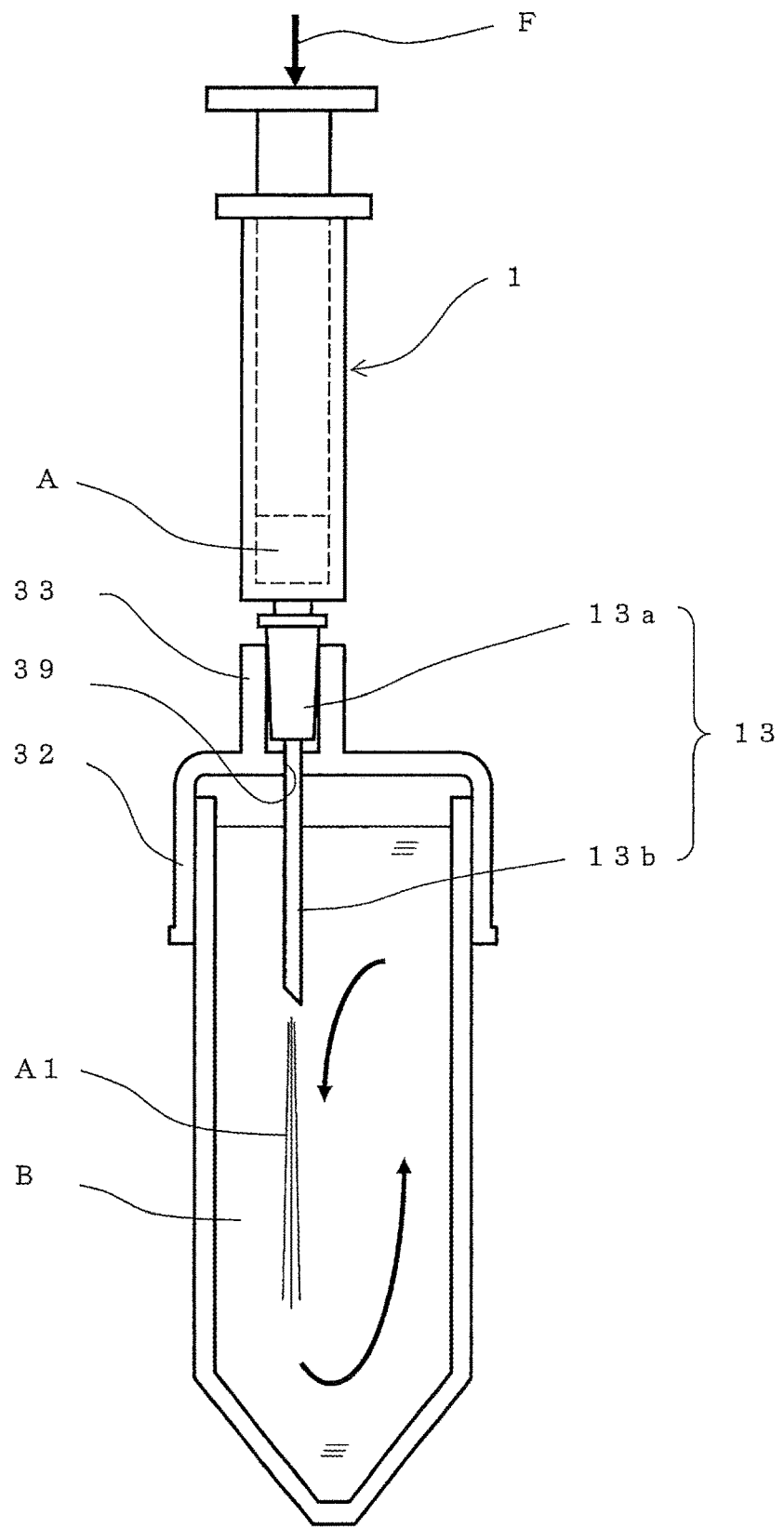
FIG. 6 is a drawing showing other specific embodiment of the production method and the production device of the present invention. In the embodiment of this drawing, the nozzle part is a component (needle) belonging to the syringe as a supply device, and the first liquid is configured to be injected in a position eccentric from the center of the container.

In the embodiments of FIG. 2, FIG. 3, FIG. 6, the shape of the bottom of the container is depicted as a cone shape that becomes narrower toward the deepest part. However, it may be a semi-spherical shape, a flat shape or the like, and is not particularly limited. From the aspects of changes in the convection state which are assumed due to the amount of liquid and viscosity, and practical handling such as improvement of recovery rate by centrifugation of cells and the like to achieve efficient sedimentation and the like, a container having a cone-shaped bottom part that becomes narrower toward the deepest part (called conical tube) of FIG. 2, FIG. 3, FIG. 6 is sometimes preferable. Examples of preferable container product include round tube 5 mL (352003), conical tube 15 mL (352095), conical tube 50 mL (352070), conical tube 175 mL (352076) and conical tube 225 mL (352075) manufactured by Japan Becton Dickinson, 15 mL centrifuge tube (MS-56150) and 50 mL centrifuge tube (MS-56500) manufactured by Sumitomo Bakelite, centrifuge tube 15 mL (2322-015), centrifuge tube 50 mL (2342-050) and centrifuge tube 230 mL (2386-230) manufactured by Asahi Glass, and the like.

The container 3 preferably has, as shown in FIG. 2, FIG. 3, FIG. 6, a body 31 having an opening, and a lid 32 to be mounted on the opening part (the opening and wall part surrounding same), since the body of a general container as a physicochemical instrument can be utilized, and from the aspect of the liquid putting in and out operation.

The material of the container is not particularly limited. Examples thereof include plastic such as polyethylene, polypropylene, polystyrene, polyethylene terephthalate, polycarbonate and the like, glass, metal and the like. The materials of the body and the lid of a container may be different from each other.

To facilitate the operation of the production device for the production method, the nozzle part is preferably provided as a part (inflow part) of the container or a part (discharge part) of the supply device.

When the nozzle part is provided as a part of the container, the nozzle part may be provided in the body of the container (not shown) or in the lid (FIG. 2, FIG. 3). The through-hole in these cases is a flow path communicating the outside of the container and the inside of the container by penetrating the nozzle part. The first liquid passes through the through-hole and injected into the second liquid in the container.

Since the body of a general container can be utilized as a physicochemical instrument, an embodiment having a nozzle part 2 provided in a lid 32 as shown in FIG. 2, FIG. 3 is preferable. An embodiment having a nozzle part 2 integrally formed in a lid 32 is preferable, and an embodiment having separately-formed parts incorporated in the lid is also preferable.

In the embodiments shown in FIG. 2, FIG. 3, the supply device 1 is a syringe, and the nozzle part 2 is provided in the lid 32 of the container 3. In both embodiments, a tubular component 33 for fitting a tip (cylindrical tip) 11*a* of the cylinder 11 of the syringe protrudes from the outer surface of the lid 32 of the nozzle part 2 toward the outside of the container.

As mentioned above, nozzle part 2 may be located in the center of the lid (FIG. 2), or located offset from the center to the periphery of the lid (FIG. 3).

When the nozzle part is offset, the opening shape of the container has a circular shape, the radius of the opening is R (mm), the distance of offset from the center to the periphery of the opening is r (mm), and a ratio of r relative to R [(r/R)×100] is about 40%-80%, the effect of the offset becomes remarkable. When the offset of the nozzle part is excessively large, the flow of the first liquid is too close to the container wall to possibly inhibit suitable stirring.

The distance from the nozzle tip to the liquid surface is preferably from 0 mm to not more than 200 mm, more preferably not more than 150 mm, further preferably not more than 85 mm.

Figure 4:
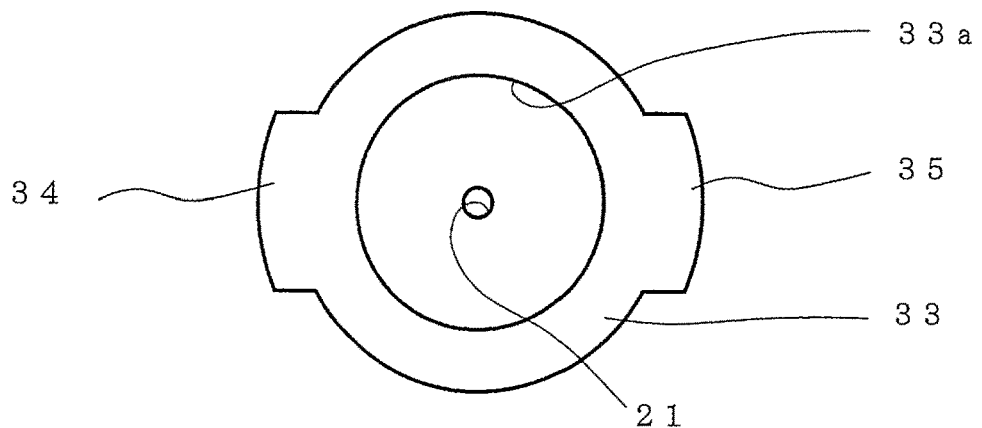
FIG. 4 shows a partially enlarged view of the nozzle part in FIG. 2, FIG. 3.
Figure 4:
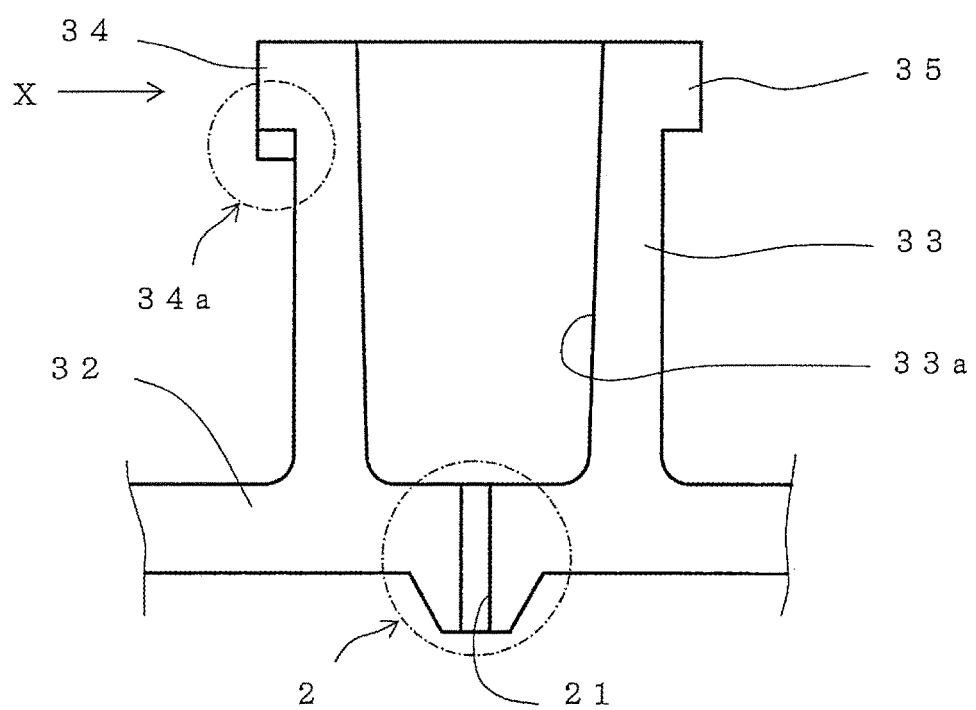
Figure 4:
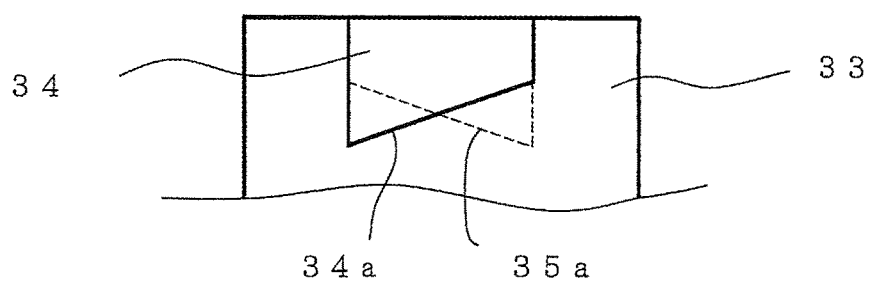

FIG. 4 is a partially-enlarged view showing in detail the nozzle part provided in the lid and the structure outside thereof in the embodiments of FIG. 2, FIG. 3.

As shown in FIG. 4(b), the tip (inside the container) of the nozzle part 2 ensures the length of the through-hole 21 and protrudes into the inside of the container so that the first liquid can leave the through-hole as a linear flow maintaining the cross section of the through-hole to the possible extent. A space may be formed between the tip of the nozzle part and the liquid surface of the second liquid contained in the container, and the tip of the nozzle part may extend long to contact the second liquid.

As a preferable option, in the embodiment of FIG. 4(a)-(c), the tip of the tubular component 33 protruding from the outer surface of the lid has protrusion parts 34, 35 protruding on the side, which are to be engaged with female threads (internal screw) on the tip of a luer-lock type syringe to fix the syringe by screwing therein. On the bottom parts of the protrusion parts 34, 35 are provided gradient 34a, 35a capable of fitting the female threads on the tip of the syringe, as shown in FIG. 4(c).

The coupling structure and sealability between the body 31 and the lid 32 of the container, the coupling structure between the tip 11a of the syringe and the tubular component 33 of the lid, and fitting and sealability of the tip 11a and the inner surface 33a of the tubular component can be set as appropriate.

Figure 5:
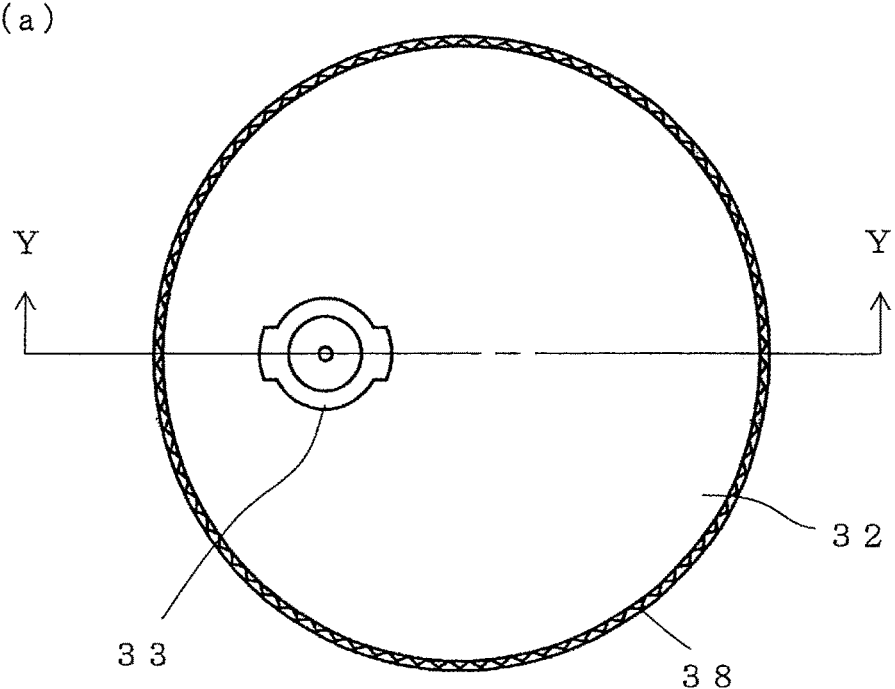
FIG. 5 shows one embodiment of the lid of the container in the production device of the present invention.
Figure 5:
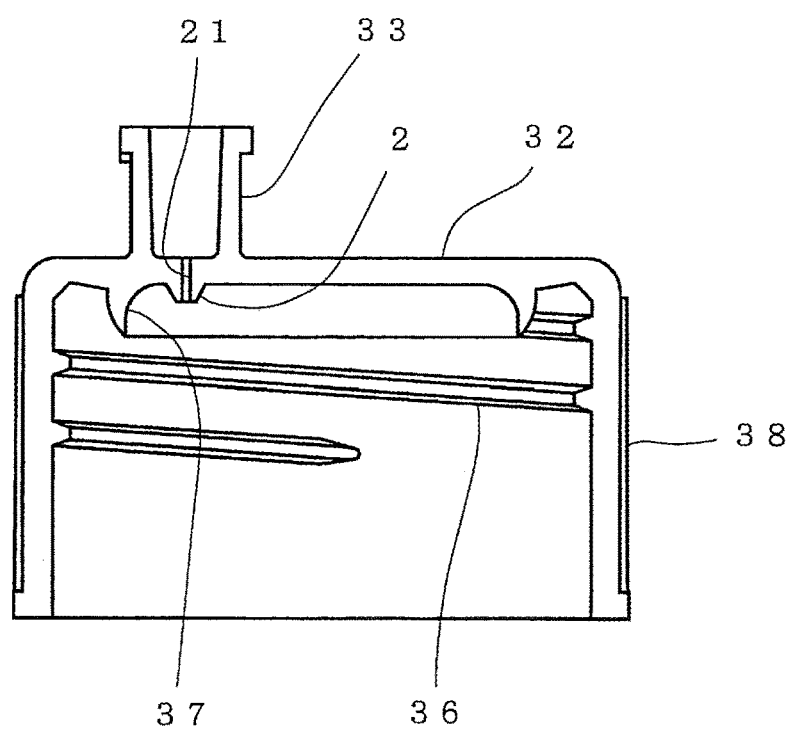

FIG. 5 shows an embodiment in which a practical structure is added to the detail of the lid shown in FIG. 3. The embodiment of this Figure has compatibility with the lid originally attached to the container so that a commercially available container for physicochemical experiments can be utilized as the body.

As shown in FIG. 5(b), a screw ridge 36 is formed in the inside of the lid 32 so that threaded engagement (screw together) with an opening part of the body of a commercially available container for physicochemical experiments can be achieved. In addition, an annular sealing part 37 for sealing the opening when the lid is threadedly engaged with the opening part of the container protrudes from the innermost surface of the inside of the lid 32. As shown in FIG. 5(a), a knurling 38 similar to the original lid is formed on the side of the outer circumference of the lid, which prevents slip in turning the lid with a hand.

In the embodiment shown in FIG. 6, a nozzle part is formed as a part of a supply device. In the embodiment of this Figure, a supply device 1 is a syringe, a nozzle part is an injection needle 13 mounted on the tip of the syringe, and an injection needle 13 has a needle base part 13a and a needle tube part 13b. The needle tube part 13a does not always need to be sharp.

In the embodiment of this Figure, the conduit in the inside of the needle tube part is the through-hole in the present invention, and the cross-sectional area thereof is 0.01 mm$^2$-5.00 mm$^2$. In the embodiment of this Figure, the tip of the needle tube part enters into the inside of the second liquid contained in the container.

The lid 32 of the container is provided with a penetrable part 39 permitting penetration of a needle tube part 13b of the injection needle 13 from the outside of the container into the container. A tubular component 33 for fitting a needle base part 13a of the injection needle protrudes from the outer surface of the lid 32 toward the outside of the container of the penetrable part 39. While the tubular component 33 is not essential, it is a preferable structure for retaining the syringe when in use.

The penetrable part 39 only needs to be formed to permit passage of the needle tube part when in use, and may be a through-hole matching with the outer diameter of the needle tube part or a weakened part or thin film part through which a needle tube part can penetrate.

When the first liquid is injected into the second liquid by the production method of the present invention, the second liquid may be stirred and the first liquid may be injected into the stirring second liquid.

Examples of the stirring method include a method of applying manual shaking, mechanical shaking (linear reciprocating motion, eccentric rotating motion and 8-shaped rotating motion), ultrasonication trembling, vortex stirring and the like to the container to stir the second liquid in the container.

The first liquid contains, as a particular compound, a polymer compound having an anionic functional group and capable of forming a structure that can suspend cells or tissues by binding via a divalent metal cation.

As the anionic functional group, carboxy group, sulfo group, phosphate group and a salt thereof can be mentioned, with preference given to carboxy group or a salt thereof. A polymer compound to be used in the present invention may contain one or more kinds selected from the group of the aforementioned anionic functional groups.

Specific preferable examples of the polymer compound to be used in the present invention include, but are not limited to, polysaccharides wherein not less than 10 monosaccharides (e.g., triose, tetrose, pentose, hexsauce, heptose etc.) are polymerized, more preferably, acidic polysaccharides having an anionic functional group. The acidic polysaccharides here is not particularly limited as long as it has an anionic functional group in the structure thereof, and includes, for example, polysaccharides having a uronic acid (e.g., glucuronic acid, iduronic acid, galacturonic acid, mannuronic acid), polysaccharides having a sulfate group or phosphate group in a part of the structure thereof, and polysaccharides having the both structures, and includes not only naturally-obtained polysaccharides but also polysaccharides produced by microorganisms, polysaccharides produced by genetic engineering, and polysaccharides artificially synthesized using an enzyme. More specifically, examples thereof include polymer compounds composed of one or two or more kinds from the group consisting of hyaluronic acid, gellan gum, deacylated gellan gum (hereinafter sometimes to be referred to as DAG), rhamsan gum, diutan gum, xanthan gum, carageenan, xanthan gum, hexuronic acid, fucoidan, pectin, pectic acid, pectinic acid, heparan sulfate, heparin, heparitin sulfate, keratosulfate, chondroitin sulfate, dermatan sulfate, rhamnan sulfate and a salt thereof. Polysaccharides are preferably hyaluronic acid, DAG, diutan gum, xanthan gum, carageenan or a salt thereof, more preferably DAG or a salt thereof. Phosphorylated DAG can also be used. The phosphorylation can be performed by a known method.

The salt here includes, for example, salts with alkali metal such as lithium, sodium, potassium; salts with alkaline earth metals such as calcium, barium, magnesium; and salts with aluminum, zinc, copper, iron, ammonium, organic base and amino acid and the like.

The weight average molecular weight of these polymer compounds (polysaccharides etc.) is preferably 10,000 to 50,000,000, more preferably 100,000 to 20,000,000, still more preferably 1,000,000 to 10,000,000. For example, the molecular weight can be measured based on pullulan by gel penetration chromatography (GPC).

In the present invention, plural kinds (preferably two kinds) of the above-mentioned polysaccharides having an anionic functional group can be used in combination. The kind of the combination of the polysaccharides is not particularly limited as long as the aforementioned structure is formed in a liquid medium by linking via a divalent metal cation. Preferably, the combination includes at least DAG or a salt thereof. That is, a preferable combination of polysaccharides contains DAG or a salt thereof, and polysaccharides other than DAG and a salt thereof (e.g., xanthan gum, alginic acid, carageenan, diutan gum, methylcellulose, locust bean gum or a salt thereof). Examples of specific combination of polysaccharides include, but are not limited to, DAG and rhamsan gum, DAG and diutan gum, DAG and xanthan gum, DAG and carageenan, DAG and xanthan gum, DAG and locust bean gum, DAG and κ-carageenan, DAG and sodium alginate, DAG and methylcellulose and the like.

The deacylated gellan gum is a linear high molecular weight polysaccharide containing 4 molecules of sugars of 1-3 bonded glucose, 1-4 bonded glucuronic acid, 1-4 bonded glucose and 1-4 bonded rhamnose as the constituent unit, which is a polysaccharide of the following formula (I) wherein $R_1$, $R_2$ are each a hydrogen atom, and n is an integer of two or more. $R_1$ may contain a glyceryl group, $R_2$ may contain an acetyl group, and the content of the acetyl group and glyceryl group is preferably not more than 10%, more preferably not more than 1%.

limited to, *Sphingomonas elodea* and microorganism obtained by altering the gene of *Sphingomonas elodea*.

In the case of deacylated gellan gum, commercially available products, for example, "KELCAOGEL (registered trade mark of CP Kelco) CG-LA" manufactured by SAN-SHO Co., Ltd., "KELCOGEL (registered trade mark of CP Kelco)" manufactured by San-Ei Gen F.F.I., Inc. and the like can be used. As a native type gellan gum, "KELCOGEL (registered trade mark of CP Kelco) HT" manufactured by San-Ei Gen F.F.I., Inc. and the like can be used.

The first liquid is generally a solution of the particular compound. While the solvent for the solution is not particularly limited as long as it can dissolve the particular compound, it is generally water or hydrophilic solvent, preferably water. In a preferable embodiment, therefore, the first liquid is an aqueous solution of the particular compound.

The concentration of the particular compound contained in the first liquid is not particularly limited as long as, upon mixing with the second liquid, the particular compounds are linked via a divalent metal cation to form a structure capable of suspending cells or tissues in the mixture, the structure is uniformly dispersed in the mixture, and further, the finally-obtained liquid medium composition containing the structure can cultivate the cells or tissue in suspension. The concentration of the particular compound in the first liquid can be calculated from the concentration of the particular compound in the medium composition capable of culturing cells or tissues in suspension and the ratio of the volume of the first liquid to the volume of the medium composition obtained as the final product, as described in detail below. For example, when the first liquid with volume $V_1$ and the second liquid with volume $V_2$ are mixed to finally obtain a liquid medium composition with volume $V_1+V_2$, the con-

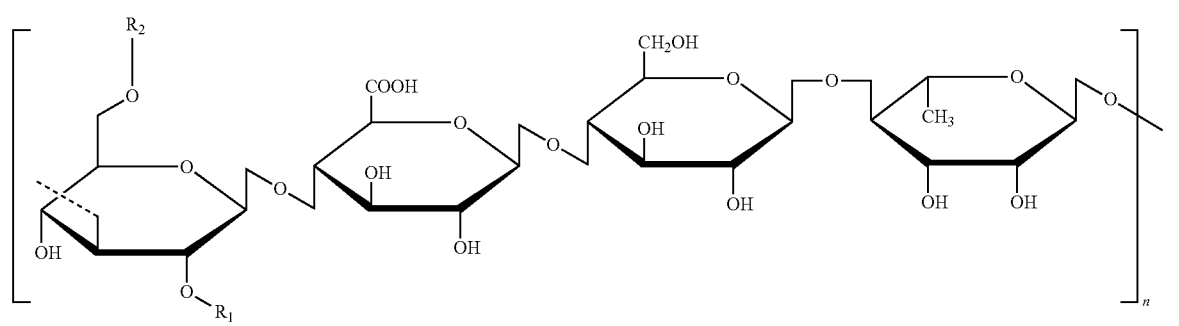

(I)

The particular compound may be obtained by a chemical synthesis method. When the particular compound is a naturally-occurring substance, it may be obtained from various plants, various animals, various microorganisms containing the compound by extraction, separation and purification by conventional techniques. For example, gellan gum can be produced by culturing producing microorganisms in a fermentation medium, recovering mucous products produced outside the bacterial cells by a general purification method, and, after the processes of drying, pulverizing and the like, powderizing the products. In the case of deacylated gellan gum, an alkali treatment should be applied when the mucous products are recovered, to deacylate the glyceryl group and the acetyl group bonded to 1-3 bonded glucose residue, and then the given products are recovered. Examples of the gellan gum-producing microorganism include, but are not centration C % (w/v) of the particular compound in the liquid medium composition can be achieved by setting the concentration of the particular compound in the first liquid to $C \times (V_1+V_2)/V_1$ % (w/v). In a specific embodiment, when DAG or a salt thereof is used as a particular compound, the concentration of DAG in the first liquid is, for example, 0.02-2.5% (w/v), preferably 0.1-2.0% (w/v), more preferably 0.5-1.5% (w/v). When the concentration of DAG exceeds 2.5% (w/v), DAG is not easily dissolved in the solvent from the viewpoint of solubility, the structures are topically formed upon mixing of the first liquid and the second liquid and entangled in a mass, thereby increasing the risk of difficult dispersing in the medium composition. On the other hand, when the concentration of DAG is lower than 0.02% (w/v), the volume of the first liquid necessary for producing the object medium composition becomes large. As a result, when a general liquid medium is adopted as the second liquid, the components derived from the liquid medium are drastically diluted when mixed with the first liquid.

The concentration of the divalent metal cation in the first liquid needs to be lower than the concentration at which the particular compound forms the structure in the first liquid. Examples of the divalent metal cation include calcium ion, magnesium ion, zinc ion, manganese ion, ferrous ion, copper ion and the like. Particularly, one or both of calcium ion and magnesium ion (hereinafter to be also referred to as "calcium ion and/or magnesium ion") contributes to the structure formation of a particular compound such as DAG and the like.

The first liquid may contain factors other than a particular compound and a solvent. Examples of the factor include, but are not limited to, physiologically acceptable buffering agent, salt, and isotonic agent.

The first liquid can be prepared by adding a particular compound to the above-mentioned solvent (e.g., water), stirring the mixture at a temperature capable of dissolving the particular compound (e.g., not less than 60° C., not less than 80° C., not less than 90° C.), and dissolving until a transparent state is formed. Using DAG subjected to divalent metal cation-exclusion treatment as mentioned above, a dissolution operation is easy since it is dissolved in water without requiring heating. Where necessary, the obtained solution of the particular compound is subjected to a divalent metal cation-exclusion treatment to render the concentration of the divalent metal cation in the solution lower than the structure-forming concentration. Where necessary, a factor other than the particular compound may be added to the solvent in advance, or a factor other than the particular compound may be added to the obtained solution of the particular compound. The first liquid is preferably sterilized. Examples of the method of the sterilization include, but are not limited to, autoclave, filtration sterilization and the like.

The second liquid contains a divalent metal cation as a linking substance. Examples of the divalent metal cation include calcium ion, magnesium ion, zinc ion, manganese ion, ferrous ion, copper ion and the like. While the kind of the divalent metal cation is not particularly limited as long as the particular compound in the first liquid is bonded via a divalent metal cation to form a structure capable of suspending cells or tissues, with preference given to calcium ion.

The second liquid is generally a solution of a linking substance (i.e., divalent metal cation). While the solvent for the solution is not particularly limited as long as it can dissolve the particular compound, it is generally water or hydrophilic solvent, preferably water. In a preferable embodiment, therefore, the second liquid is an aqueous solution of a linking substance (i.e., divalent metal cation).

The second liquid contains a divalent metal cation at a concentration sufficient for the particular compound in the first liquid to form the structure when the first liquid and the second liquid are mixed. For example, when calcium ion or magnesium ion is used as the linking substance, the concentration of the calcium ion or magnesium ion in the second liquid is generally not less than 0.001 mM, preferably not less than 0.01 mM. The upper limit of the concentration of the divalent metal cation in the second liquid is theoretically the concentration of a saturated solution (i.e., solubility). When the concentration of the divalent metal cation is too high, the cells and the like to be cultured in the produced medium composition may be adversely influenced. Therefore, for example, when calcium ion or magnesium ion is used as the linking substance, the upper limit of the concentration of the calcium ion or magnesium ion in the second liquid is generally not more than 100 mM, preferably not more than 10 mM. When the second liquid contains both calcium ion and magnesium ion, the total concentration of these ions is not more than 100 mM, preferably not more than 10 mM.

The second liquid may contain factors other than a linking substance (i.e., divalent metal cation) and the solvent. Examples of the factor include medium constituent components suitable for culturing the intended cells. Examples of the medium constituent component include, but are not limited to, buffering agent (carbonate buffer, phosphate buffer, HEPES etc.), inorganic salts (NaCl etc.), various amino acids, various vitamins (choline, folic acid etc.), saccharides (glucose etc.), antioxidants (monothioglycerol etc.), pyruvic acid, fatty acids, serum, antibiotics, insulin, transferrin, lactoferrin, cholesterol, various cytokines, various hormones, various growth factors, various extracellular matrices, and the like. The second liquid is preferably sterilized. Examples of the sterilization method include, but are not limited to, autoclave, filtration sterilization and the like.

In a preferable embodiment, the second liquid is a liquid medium containing a divalent metal cation (preferably, calcium ion and/or magnesium ion) at the structure-forming concentration. That is, the second liquid contains, in addition to a divalent metal cation (preferably, calcium ion and/or magnesium ion) at the structure-forming concentration and water, medium constituent components suitable for culturing the intended cells. The concentration of the calcium ion in a generally-used liquid medium for cell culture is about 0.1-2.0 mM, and the concentration of the magnesium ion is about 0.1-1.0 mM, which are sufficient for formation of the structure by a particular compound such as DAG and the like.

In this embodiment, the intended liquid medium composition containing a structure in which particular compounds contained in the first liquid are linked via a linking substance contained in the second liquid can be obtained immediately by mixing the first liquid and the second liquid according to the production method of the present invention.

The second liquid may not contain a part or the whole of the medium constituent component for cell culture. In this case, the intended liquid medium composition can be obtained by, in the production method of the present invention, mixing the first liquid and the second liquid to give a mixture containing a structure in which particular compounds contained in the first liquid are linked via a linking substance contained in the second liquid and adding a part or the whole of the above-mentioned liquid medium constituent component for cell culture to the mixture.

The liquid medium composition that can be obtained by the production method of the present invention contains a structure in which particular compounds contained in the first liquid are linked via a linking substance (i.e., divalent metal cation) contained in the second liquid, wherein the structures are uniformly dispersed in the medium composition. Therefore, using the medium composition, cells and tissues can be cultured while maintaining the suspended state.

The type of organism from which cells or tissues to be cultured are derived is not particularly limited, and may be not only animals (insect, fish, amphibian, reptiles, birds, pancrustacea, hexapoda, mammals and the like) but also plants.

In one embodiment, the cell to be cultured is an anchorage dependent cell. Using the liquid medium composition that can be obtained by the production method of the present invention, anchorage dependent cells can be cultured while maintaining a suspended state, without using a carrier to be the anchorage.

Suspending of cells and/or tissues in the present invention refers to a state where cells and/or tissues may contact the bottom surface but do not adhere to a culture container (non-adhesive). Furthermore, in the present invention, when the cells and/or tissues are proliferated, differentiated or maintained, the state where the cells and/or tissues are uniformly dispersed and suspended in the liquid medium composition in the absence of a pressure on or vibration of the liquid medium composition from the outside or shaking, rotating operation and the like is referred to as "static suspension", and culturing of the cells and/or tissues in such condition is referred to as "static suspension culture". In the "static suspension", the duration of suspending includes not less than 5 min, not less than 1 hr, not less than 24 hr, not less than 48 hr, not less than 7 days and the like, though the duration is not limited thereto as long as the suspended state is maintained.

The medium composition that can be obtained by the production method of the present invention permits static suspension of cells and/or tissues at least on one point in the temperature range (e.g., 0-40° C.) capable of maintaining or culturing cells or tissues. The medium composition to be used in the present invention permits static suspension of cells and/or tissues at least at one point in the temperature range of preferably 25-37° C., most preferably 37° C.

Whether or not static suspension is possible can be evaluated by, for example, uniformly dispersing the cells to be cultured in a medium composition to be evaluated at a concentration of $2 \times 10^4$ cells/ml, injecting 10 ml thereof in a 15 ml conical tube, standing the tube for at least not less than 5 min (e.g., not less than 1 hr, not less than 24 hr, not less than 48 hr, not less than 7 days) at 37° C., and observing whether the suspended state of the cells is maintained. When not less than 70% of the total cells are in a suspended state, it is concluded that the suspended state was maintained. Polystyrene beads (Size 500-600 μm, manufactured by Polysciences Inc.) may be used for evaluation instead of the cells In a preferable embodiment, in the liquid medium composition that can be obtained by the production method of the present invention, the viscosity thereof is not substantially increased by the contained above-mentioned structure, since it contains the above-mentioned structure. The terms "not substantially increasing the viscosity of the liquid" means that the viscosity of the liquid does not exceed 8 mPa·s. In this case, the viscosity of the liquid (that is, the viscosity of the liquid medium composition that can be obtained by the production method of the present invention) is not more than 8 mPa·s, preferably not more than 4 mPa·s, more preferably not more than 2 mPa·s at 37° C. The viscosity of the liquid containing the structure can be measured under 37° C. conditions and using an E-type viscosity meter (manufactured by Toki Sangyo Co., Ltd., TV-22 type viscosity meter, model: TVE-22 L, corn rotor: standard rotor 1°34'×R24, rotating speed 100 rpm).

The concentration of the particular compound in a liquid medium composition that can be obtained by the production method of the present invention depends on the kind of the particular compound, and can be appropriately determined within the range where the particular compound can form the aforementioned structure in a liquid medium composition, and can uniformly suspend (preferably statically suspend) the cells and/or tissues (preferably, without substantially increasing the viscosity of the liquid). In the case of DAG, it is 0.001% to 1.0% (w/v), preferably 0.003% to 0.5% (w/v), more preferably 0.005% to 0.3% (w/v), further preferably 0.01% to 0.05% (w/v), most preferably 0.01% to 0.03% (w/v). In the case of xanthan gum, it is 0.001% to 5.0% (w/v), preferably 0.01% to 1.0% (w/v), more preferably 0.05% to 0.5% (w/v), most preferably 0.1% to 0.2% (w/v). In the case of κ-carrageenan and locust bean gum mixture system, the total of the both compounds is 0.001% to 5.0% (w/v), preferably 0.005% to 1.0% (w/v), more preferably 0.01% to 0.1% (w/v), most preferably 0.03% to 0.05% (w/v). In the case of a native type gellan gum, it is 0.05% to 1.0% (w/v), preferably 0.05% to 0.1% (w/v).

When plural kinds (preferably two kinds) of the above-mentioned polysaccharides are used in combination as a particular compound, the concentration of the polysaccharides can form the aforementioned structure in a liquid medium composition, and can uniformly suspend (preferably statically suspend) the cells and/or tissues (preferably without substantially increasing the viscosity of the liquid). For example, when a combination of DAG or a salt thereof and polysaccharide other than DAG and a salt thereof is used, the concentration of DAG or a salt thereof is, for example, 0.005-0.02% (w/v), preferably 0.01-0.02% (w/v), and the concentration of polysaccharide other than DAG and a salt thereof is, for example, 0.0001-0.4% (w/v), preferably 0.005-0.4% (w/v), more preferably 0.1-0.4% (w/v). Specific examples of the combination of the concentration range include the following.

DAG or a salt thereof: 0.005-0.02% (preferably 0.01-0.02%) (w/v)
polysaccharide other than DAG
xanthan gum: 0.1-0.4% (w/v)
sodium alginate: 0.0001-0.4% (w/v) (preferably 0.1-0.4% (w/v))
native gellan gum: 0.0001-0.4% (w/v)
locust bean gum: 0.1-0.4% (w/v)
methylcellulose: 0.1-0.4% (w/v) (preferably 0.2-0.4% (w/v))
carageenan: 0.05-0.1% (w/v)
diutan gum: 0.05-0.1% (w/v)

The concentration can be calculated by the following formula.

Concentration[% (w/v)]=weight (g) of particular compound/volume (mL) of medium composition×100

In a preferable embodiment, DAG or a salt thereof is used as the particular compound, and calcium ion is used as the linking substance. The first liquid is an aqueous solution of DAG or a salt thereof. The concentration of DAG in the aqueous solution is generally 0.05-1.5% (w/v), preferably 0.1-1.2% (w/v), more preferably 0.5-1.0% (w/v). The second liquid is a liquid medium containing calcium ion. The concentration of calcium ion in the liquid medium is a concentration at which DAG forms a structure, and is generally about 0.1-2.0 mM. The volume ratio of the first liquid and the second liquid to be mixed is (first liquid: second liquid)=(0.5-10:100), preferably (1-5:100), more preferably (1.5-3:100). The volume of the first liquid is, for example, 0.1-20 mL, preferably 0.3-12 mL, more preferably 0.6-6 mL. The volume of the second liquid is, for example, 1-1000 mL, preferably 10-500 mL, more preferably 40-200 mL. The concentration of DAG in the resulting liquid medium composition is preferably 0.01%-0.05% (w/v), most preferably 0.01%-0.03% (w/v).

Since the liquid medium composition contains a structure, in which DAG is linked via a calcium ion, uniformly dispersed therein, the cells and/or tissues can be uniformly suspended (preferably statically suspended) without substantially increasing the viscosity.

Using the liquid medium composition obtained by the production method of the present invention, cells and/or tissues can be cultured in a suspended state without an operation such as shaking, rotation and the like having a risk of causing damage and loss of functions of cells and tissues. Furthermore, using the medium composition, the medium can be exchanged easily during culture, and the cultured cells and/or tissues can also be recovered easily. Using the medium composition, adhesive cells can be prepared efficiently in a large amount without impairing the function thereof, since cells conventionally required to be cultured on a plate in a single layer in an adhered state to a cell container can be cultured in a suspended state.

Now, the kit of the present invention is explained. The kit of the present invention is, as shown in FIG. 7, a set of assembly of the constituent elements for practicing the above-mentioned production method of the present invention.

As shown in FIG. 7, the kit of the present invention contains the first container K1 containing the above-mentioned first liquid, and is configured to at least comprise syringe K2 as a supply device 1 for feeding out the first liquid explained above and the second container K3 as a container 3 explained by reference to FIG. 2-FIG. 5. The second container K3 is, as explained above as regards container 3, a container having lid K32 with a nozzle part and body K31, and further has, on the container outside side of the nozzle part, a tubular component to fit the tip of the syringe, protruding from the outer surface of the lid.

The first container K1 is not limited as to the material and size as long as it can contain the above-mentioned first liquid only in an amount required by a user and can deliver same to the user. The first container K1 is preferably in an embodiment having a container body and a lid for closing the opening of the container body, and the lid is preferably in an embodiment threadedly engaged with the container body.

The second liquid may be provided in a kit, or may be a liquid medium generally used by a user.

In a preferable embodiment of the kit of the present invention, as shown in FIG. 7, the second container K3 is further equipped with a sealing lid K32 without a nozzle part, which is configured to be able to seal the inside of the body K31 of the container. The sealing lid K32 is compatible with the lid K32 of the container and can be mounted on the opening part of the body K31 of the container.

Provision of the sealing lid K32 enables production of a liquid medium composition in the body K31 of the container by using lid K32 having a nozzle part, and sealing the liquid medium composition in body K31 of the container.

When the body K31 of the container is a commercially available product, the sealing lid K32 may be a lid originally attached to the container body of the commercially available product.

In a preferable embodiment of the kit of the present invention, as shown in FIG. 7, a tubular component K21 is further equipped, which can be mounted on the tip of the above-mentioned syringe K2. The tubular component is a suction tube used by inserting in the first container to aspirate the first liquid into the syringe. The tubular component has a thin-tube part having an outer diameter permitting insertion into the first container K1 and a length permitting aspiration of the first liquid from the inside of the first container, as well as a connecting part mountable on the tip of the cylinder of the syringe, at one end of the thin-tube part. The tubular component may be an injection needle, but an economical resin molded part is preferable.

EXAMPLES

Various Experimental Examples evaluating the production device and production method of the present invention are shown below. The "Comparative Example" in each of the following Experimental Examples is an Experimental Example conducted according to the technical idea of the present invention to investigate preferable numerical values and conditions of the present invention, and does not refer to the Prior Art.

The concentration of divalent cation in the medium used in each test is as shown in the following Table 1.

TABLE 1

| | ion concentration | | | | |
|---|---|---|---|---|---|
| medium | calcium [mM] | magnesium [mM] | copper [nM] | iron [µM] | zinc [µM] |
| DMEM (high glucose) | 1.8 | 0.81 | — | — | — |
| DMEM-F12 | 1.1 | 0.71 | 5.2 | 1.6 | 1.5 |
| Ham's F12 | 0.3 | 0.6 | 10 | 3.0 | 3.0 |
| EMEM | 1.8 | 0.81 | — | — | — |
| RPMI | 0.9 | 0.41 | — | — | — |

Experimental Example 1: Test for Evaluation of the Production Device and Production Method of the Present Invention One embodiment of the production device of the present invention was produced, the production method of the present invention was carried out using same, and the results of the test observing the dispersion state of the structure in the obtained medium composition are shown in the following. As a Comparative Example, the test results when the flow rate of the injection of the first liquid was decreased are shown.

In Examples 1-9 and Comparative Examples 1-16, a particular compound was deacylated gellan gum, the first liquid was a deacylated gellan gum solution, and a liquid medium containing calcium ion and magnesium ion as a linking substance to link the deacylated gellan gum to form the structure was the second liquid.

[Specifications of Production Device]

In Examples 1-9 and Comparative Examples 1-16, a production device of the type shown in FIG. 3 was produced.

As a container, the body part of a commercially available conical tube with capacity 225 mL (225000 mm$^3$) or capacity 50 mL (50000 mm$^3$) (manufactured by SUMITOMO BAKELITE) was used, and a lid matching same as shown in FIG. 5 was produced. The bore diameter of the through-hole was 0.5 mm. Therefore, the cross-sectional area of the through-hole was about 0.2 mm$^2$.

As a supply device, a disposable syringe with capacity 5 mL (5000 mm$^3$) or capacity 1 mL (1000 mm$^3$) was used, and a tip of the cylinder of the syringe could be coupled by being fitted into the cylindrical part 33 protruding from the outside of the lid.

[Preparation of First Liquid]

Deacylated gellan gum (KELCOGEL CG-LA, manufactured by Sansho Co., Ltd.) was suspended in ultra pure water (Milli-Q water) to 0.75% (w/v), dissolved by stirring with heating at 90° C., and this aqueous solution was autoclave sterilized at 121° C. for 20 min.

[Preparation of Liquid Medium Composition Product]

As the second liquid, Dulbecco's Modified Eagles's Medium (DMEM high glucose, manufactured by Wako Pure Chemical Industries, Ltd.) (200 mL) was contained in a 225 mL conical tube (manufactured by SUMITOMO BAKE-LITE) and cooled to 4° C. The concentration of calcium ion in DMEM was 1.80 mM, and the magnesium ion concentration was 0.8 mM.

The cap of the conical tube filled with the second liquid cooled to 4° C. was removed, and a lid produced as the production device of the present invention was mounted.

The tip of the disposable syringe filled with the above-mentioned sterilized aqueous deacylated gellan gum solution (4 mL, 4000 mm$^3$) was fitted into the cylindrical part of the lid to form connection, whereby the production device of the present invention, which is of the type shown in FIG. 3, was constituted.

In this state, plunger of the syringe was pushed by human power, and the deacylated aqueous gellan gum solution in the syringe was injected into the container by moving same at the constant speed to give a medium composition.

The conditions of concentration and volume of each liquid, flow rate of the first liquid injection and the like were changed to give Examples 1-9 and Comparative Examples 1-16. The flow rate of the first liquid in each Example was achieved by adjusting the moving time of the syringe plunger. In Examples 3, 5, 8, and Comparative Examples 3, 5, 10, 14, 16, the first liquid was injected into the second liquid in a stirring state in a whirlpool manner by using a vortex mixer (2500 rpm).

After injection, the adapter cap was changed to a cap of a conical tube, and the tube was tightly sealed.

[Evaluation]

Polystyrene beads (diameter 500-600 μm, manufactured by Polysciences Inc.) for simulating suspended cells were added to the produced medium composition and stirred, and the dispersed state of the beads in the liquid was confirmed by visual observation 10 min after discontinuation of the stirring.

When the structure is appropriately finely dispersed in the liquid, the beads are also dispersed and remain suspended in the liquid. On the other hand, when dispersion of the structure is not sufficient, the beads also settle down accordingly.

When the structure is appropriately finely dispersed in the liquid, the structure cannot be recognized by visual observation. On the other hand, when the structure forms a string or gathers, the structure can be recognized by visual observation as a material scattering the light, or a transparent amorphous string material visually observed due to the refraction of light.

The test conditions, dispersion state of beads in the resulting products, and the state of the structures in Examples 1-9 and Comparative Examples 1-16 are shown in Table 2. In Table 2, the dispersion state of the beads is shown with ○ for preferably dispersed and suspended state, Δ for dispersed but partly sedimented state, and x for the state of sedimentation of all beads.

Whether the structure cannot be visually recognized (considered to be appropriately finely dispersed), or is string or mass is shown with ○, Δ, x as follows.

○ shows that the structure cannot be visually recognized as a suspended material, as in commercially available liquid medium composition FCeM (registered trade mark).

Δ is a material that scatters light when held to light, or transparent amorphous string material permitting visual observation of suspended state due to the refraction of light.

x is a state permitting visual observation of suspended state or formation of sediment of the structure as a clear fibrous precipitate.

TABLE 2

| | second liquid B | | | first liquid A | | | evaluation results | |
|---|---|---|---|---|---|---|---|---|
| | kind | amount added [mL] | stirring [rpm] | concentration [%] | amount added [mL] | flow rate [mL/s] | suspended state of beads | state of structure |
| Ex. 1 | DMEM | 200 | 0 | 0.75 | 4 | 5.0 | ○ | ○ |
| Ex. 2 | DMEM | 200 | 0 | 0.5 | 6 | 4.3 | ○ | ○ |
| Ex. 3 | DMEM | 200 | 2500 | 1 | 3 | 4.3 | ○ | ○ |
| Ex. 4 | DMEM | 200 | 0 | 1 | 3 | 4.3 | ○ | ○ |
| Ex. 5 | DMEM | 40 | 2500 | 1 | 0.6 | 3.0 | ○ | ○ |
| Ex. 6 | DMEM | 40 | 0 | 1 | 0.6 | 3.0 | ○ | ○ |
| Ex. 7 | DMEM | 200 | 0 | 0.75 | 4 | 2.0 | ○ | ○ |
| Ex. 8 | DMEM | 200 | 2500 | 1 | 3 | 2.0 | ○ | ○ |
| Ex. 9 | DMEM | 200 | 0 | 1 | 3 | 1.7 | ○ | ○ |
| Com. Ex. 1 | DMEM | 40 | 0 | 1 | 0.6 | 1.5 | Δ | Δ |
| Com. Ex. 2 | DMEM | 200 | 0 | 0.5 | 6 | 1.3 | ○ | Δ |
| Com. Ex. 3 | DMEM | 40 | 2500 | 1 | 0.6 | 1.2 | Δ | Δ |
| Com. Ex. 4 | DMEM | 40 | 0 | 1 | 0.6 | 1.2 | Δ | Δ |
| Com. Ex. 5 | DMEM | 200 | 2500 | 1 | 3 | 1.0 | Δ | x |
| Com. Ex. 6 | DMEM | 200 | 0 | 0.75 | 4 | 0.78 | Δ | Δ |
| Com. Ex. 7 | DMEM | 200 | 0 | 0.5 | 6 | 0.76 | ○ | Δ |
| Com. Ex. 8 | DMEM | 200 | 0 | 0.5 | 6 | 0.66 | Δ | x |
| Com. Ex. 9 | DMEM | 200 | 0 | 1 | 3 | 0.65 | Δ | x |

TABLE 2-continued

|  | second liquid B | | | first liquid A | | | evaluation results | |
|---|---|---|---|---|---|---|---|---|
|  | kind | amount added [mL] | stirring [rpm] | concentration [%] | amount added [mL] | flow rate [mL/s] | suspended state of beads | state of structure |
| Com. Ex. 10 | DMEM | 40 | 2500 | 1 | 0.6 | 0.60 | Δ | x |
| Com. Ex. 11 | DMEM | 40 | 0 | 1 | 0.6 | 0.60 | x | x |
| Com. Ex. 12 | DMEM | 200 | 0 | 0.5 | 6 | 0.55 | x | x |
| Com. Ex. 13 | DMEM | 200 | 0 | 0.75 | 4 | 0.53 | x | x |
| Com. Ex. 14 | DMEM | 200 | 2500 | 1 | 3 | 0.47 | x | x |
| Com. Ex. 15 | DMEM | 200 | 0 | 0.75 | 4 | 0.37 | x | x |
| Com. Ex. 16 | DMEM | 40 | 2500 | 1 | 0.6 | 0.16 | Δ | x |

From the results of Table 2, it was found that the stirring state and the non-stirring state of the second liquid show no difference. As is clear from Comparative Examples 1-16, even when the same through-hole is used, a smaller flow rate of the first liquid results in lower flow velocity, and dispersion of fine structure is not achieved. From the above, it was found that a medium composition in which a structure is preferably dispersed can be obtained by simple injection according to the production method of the present invention.

Experimental Example 2: Test Relating to Bore Diameter of Through-Hole of Nozzle Part In Experimental Example 2, the same amount of the first liquid is injected by the same pressing force from a syringe with the same specifications, and changes in the flow rate and flow velocity, and the dispersed state (suspending property) of the beads and the state of the structure (precipitate) as in the above-mentioned Experimental Example 1 when the bore diameter of the through-hole of the nozzle part was stepwisely changed were evaluated.

The first liquid, syringe, the second liquid, and conical tube used were the same as those in the above-mentioned Experimental Example 1. In Experimental Example 2, to stepwisely change the bore diameter of the through-hole of the nozzle part, injection needles of various gauges (inner diameter) were mounted on the syringe tip. That is, in this Experimental Example, the inner passage of the injection needle is the through-hole. The criteria of the evaluation of the dispersed state (suspending property) of the beads and the state of the structure (precipitate) were the same as those in the above-mentioned Experimental Example 1.

In Experimental Example 2, an injection needle with gauge number 18 was used in Example 10, and the same gauge number and longer addition time (smaller flow rate) was used in Comparative Example 17.

Similarly, an injection needle with gauge number 20 was used in Example 11, and the same gauge number and longer addition time (smaller flow rate) was used in Comparative Examples 18, 19.

Similarly, an injection needle with gauge number 22 was used in Example 12, and the same gauge number and longer addition time (smaller flow rate) was used in Comparative Examples 20, 21.

Furthermore, as a reference test, an injection needle with a small bore diameter gauge number 25 was used and tests by changing the addition time were carried out as Comparative Examples 21, 22, 23.

The dispersed state (suspending action) of beads and the state of structure in each Experimental Example (Example, Comparative Example) is shown in Table 3.

TABLE 3

|  | gauge | inner diameter of through-hole [mm] | cross section of through-hole [mm$^2$] | injecttion time [second] | amount added [mm$^3$] | flow rate [mm$^3$/sec] | flow velocity [mm/sec] | suspended state of beads | precipitate | note relating to precipitate |
|---|---|---|---|---|---|---|---|---|---|---|
| Ex. 10 | 18 | 0.94 | 0.69 | 0.2 | 800 | 4000 | 5767 | ○ | ○ | no precipitation |
| Com. Ex. 17 | 18 | 0.94 | 0.69 | 1.4 | 800 | 571 | 824 | x | x | large amount of precipitate |
| Ex. 11 | 20 | 0.66 | 0.34 | 0.2 | 800 | 4000 | 11698 | ○ | ○ | no precipitation |
| Com. Ex. 18 | 20 | 0.66 | 0.34 | 0.6 | 800 | 1333 | 3899 | Δ | Δ | fibrous precipitate |
| Com. Ex. 19 | 20 | 0.66 | 0.34 | 1.5 | 800 | 533 | 1560 | x | x | large amount of precipitate |
| Ex. 12 | 22 | 0.48 | 0.18 | 0.3 | 800 | 2667 | 14744 | ○ | ○ | no precipitation |
| Com. Ex. 20 | 22 | 0.48 | 0.18 | 0.6 | 800 | 1333 | 7372 | ○ | Δ | precipitated |

TABLE 3-continued

| | gauge | inner diameter of through-hole [mm] | cross section of through-hole [mm$^2$] | injecttion time [second] | amount added [mm$^3$] | flow rate [mm$^3$/sec] | flow velocity [mm/sec] | suspended state of beads | precipitate | note relating to precipitate |
|---|---|---|---|---|---|---|---|---|---|---|
| Com. Ex. 21 | 22 | 0.48 | 0.18 | 1.7 | 800 | 471 | 2602 | x | x | large amount of precipitate |
| Com. Ex. 22 | 25 | 0.32 | 0.08 | 1.6 | 800 | 500 | 6220 | ○ | Δ | gel-like suspending matter |
| Com. Ex. 23 | 25 | 0.32 | 0.08 | 2.5 | 800 | 320 | 3981 | ○ | Δ | gel-like suspending matter |
| Com. Ex. 24 | 25 | 0.32 | 0.08 | 3.3 | 800 | 242 | 3016 | Δ | x | many precipitates produced |

In the following Table 4, the order of description in the above-mentioned Table 3 was changed, and described separately in Examples 10-12 and Comparative Examples 17-24.

TABLE 4

| | gauge | inner diameter of through-hole [mm] | cross section of through-hole [mm$^2$] | injection time [second] | amount added [mm$^3$] | flow rate [mm$^3$/sec] | flow velocity [mm/sec] | suspended state of beads | precipitate | note relating to precipitate |
|---|---|---|---|---|---|---|---|---|---|---|
| Ex. 10 | 18 | 0.94 | 0.69 | 0.2 | 800 | 4000 | 5767 | ○ | ○ | no precipitation |
| Ex. 11 | 20 | 0.66 | 0.34 | 0.2 | 800 | 4000 | 11698 | ○ | ○ | no precipitation |
| Ex. 12 | 22 | 0.48 | 0.18 | 0.3 | 800 | 2667 | 14744 | ○ | ○ | no precipitation |
| Com. Ex. 17 | 18 | 0.94 | 0.69 | 1.4 | 800 | 571 | 824 | x | x | large amount of precipitate |
| Com. Ex. 18 | 20 | 0.66 | 0.34 | 0.6 | 800 | 1333 | 3899 | Δ | Δ | fibrous precipitate |
| Com. Ex. 19 | 20 | 0.66 | 0.34 | 1.5 | 800 | 533 | 1560 | x | x | large amount of precipitate |
| Com. Ex. 20 | 22 | 0.48 | 0.18 | 0.6 | 800 | 1333 | 7372 | ○ | Δ | precipitated |
| Com. Ex. 21 | 22 | 0.48 | 0.18 | 1.7 | 800 | 471 | 2602 | x | x | large amount of precipitate |
| Com. Ex. 22 | 25 | 0.32 | 0.08 | 1.6 | 800 | 500 | 6220 | ○ | Δ | gel-like suspending matter |
| Com. Ex. 23 | 25 | 0.32 | 0.08 | 2.5 | 800 | 320 | 3981 | ○ | Δ | gel-like suspending matter |
| Com. Ex. 24 | 25 | 0.32 | 0.08 | 3.3 | 800 | 242 | 3016 | Δ | x | many precipitates produced |

As is clear from the results of Table 4, even when the inner diameter of the through-hole is the same, good bead dispersed state (good suspending property) and good structure state (no precipitation) cannot be satisfied simultaneously unless the first liquid is injected at an appropriate flow rate.

As is also clear from the results of Comparative Examples 17-24, even when the cross section area of the through-hole is within the range of the present invention, good bead dispersed state (good suspending property) and good structure state (no precipitation) cannot be satisfied simultaneously when the first liquid is added to the second liquid at a flow rate of not more than 1.7 mL/sec.

Experimental Example 3: Test Relating to Inject Direction of the First Liquid In Experimental Example 2, in injecting the first liquid from the syringe into the container, whether the dispersed state of the beads (suspending property) varies between an injection direction of from the top to the lower side, and an injection direction of from the bottom to the upper side by setting the container upside down, was evaluated.

The first liquid, syringe, second liquid, and conical tube used were the same as those in the above-mentioned Experimental Example 1.

The dispersed state (suspending action) of beads in each Experimental Example is shown in Table 5.

TABLE 5

| No. | second liquid kind | temperature [° C.] | amount [mL] | amount of first liquid [mL] | DAG final concentration [wt %] | container, syringe orientation when mixing | suspending action | note |
|---|---|---|---|---|---|---|---|---|
| a1 | DEEM-h | 4 | 40 | 0.8 | 0.015 | 50 mL tube, 1 mL syringe injected from top | ○ | good |
| a2 | DEEM-h | 4 | 40 | 0.8 | 0.015 | 50 mL tube, 2.5 mL syringe injected from bottom | ○ | good |
| a3 | DEEM-h | 4 | 40 | 0.8 | 0.015 | 50 mL tube, 1 mL syringe injected from bottom | ○ | good |
| a4 | DEEM-h | 4 | 50 | 1.0 | 0.015 | 50 mL tube, 1 mL syringe injected from top | ○ | many fine bubbles |
| a5 | DEEM-h | 4 | 50 | 1.0 | 0.015 | 50 mL tube, 2.5 mL syringe injected from top | ○ | many fine bubbles |
| a6 | DEEM-h | 4 | 50 | 1.0 | 0.015 | 50 mL tube, 1 mL syringe injected from bottom | ○ | good |
| a7 | DEEM-h | 4 | 40 | 0.8 | 0.015 | 50 mL tube, 2.5 mL syringe injected from top | ○ | many fine bubbles |
| a8 | DEEM-h | 4 | 50 | 1.0 | 0.015 | 50 mL tube, 2.5 mL syringe injected from bottom | ○ | good |

As is clear from the results of Table 5, it was found that the production method of the present invention affords a preferable suspending action irrespective of the injection direction.

Experimental Example 4: Test Relating to Shape of Container, Distance from Outlet Opening of Nozzle Part to Liquid Surface In Experimental Example 4, an influence of the ratio of container length (size in depth direction) L and outer diameter D of container (aspect ratio L/D), the ratio of the second liquid depth Z maintained in the container and inner diameter d of container (aspect ratio Z/d), and the distance from outlet opening of the nozzle part to liquid surface on the suspending property during mixing was examined.

The dispersed state (suspending action) of beads in each Experimental Example is shown in Table 6.

TABLE 6

| No. | second liquid kind | second liquid amount | outer dimensions of container body capacity type (mL) | outer dimensions of container body length L (mm) | outer dimensions of container body outer diameter D (mm) | L/D | DAG liquid concentration (wt %) | DAG liquid amount added (mm³) | addition method | stirring (rpm) | distance from discharge opening to liquid surface (mm) | inner size of liquid immersion part depth Z (mm) | inner size of liquid immersion part inner diameter d (mm) | Z/d | floatability | note |
|---|---|---|---|---|---|---|---|---|---|---|---|---|---|---|---|---|
| b1 | DMEM (HG) | 5000 | 15 | 118 | 16 | 7.4 | 1 | 75 | syringe + tip needle | 2600 | 73 | 43 | 14 | 3.1 | ○ | high LD container |
| b2 | DMEM (HG) | 10000 | 50 | 115 | 28 | 4.1 | 0.75 | 200 | container with nozzle part | 0 | 85 | 28 | 26 | 1.1 | x | distance to liquid surface x |
| b3 | DMEM (HG) | 20000 | 50 | 115 | 28 | 4.1 | 0.75 | 400 | container with nozzle part | 0 | 67 | 46 | 26 | 1.8 | ○ | distance to liquid surface ○ |
| b4 | DMEM (HG) | 30000 | 50 | 115 | 28 | 4.1 | 0.75 | 600 | container with nozzle part | 0 | 48 | 65 | 26 | 2.5 | ○ | distance to liquid surface ○ |
| b5 | DMEM (HG) | 40000 | 50 | 115 | 28 | 4.1 | 0.75 | 800 | container with nozzle part | 0 | 30 | 83 | 26 | 3.2 | ○ | distance to liquid surface ○ |
| b6 | DMEM (HG) | 50000 | 50 | 115 | 28 | 4.1 | 0.75 | 1000 | container with nozzle part | 0 | 12 | 101 | 26 | 3.9 | ○ | distance to liquid surface ○ |
| b7 | DMEM (HG) | 140000 | 225 | 138 | 60 | 2.3 | 1 | 2100 | container with nozzle part | 2500 | 64 | 72 | 58 | 1.2 | x | low LD container and liquid surface distance |
| b8 | DMEM (HG) | 160000 | 225 | 138 | 60 | 2.3 | 1 | 2400 | container with nozzle part | 2500 | 56 | 80 | 58 | 1.4 | ○ | low LD container and liquid surface distance |
| b9 | DMEM (HG) | 180000 | 225 | 138 | 60 | 2.3 | 1 | 2700 | container with nozzle part | 2500 | 49 | 87 | 58 | 1.5 | ○ | low LD container and liquid surface distance |
| b10 | DMEM (HG) | 200000 | 225 | 138 | 60 | 2.3 | 1 | 3000 | container with nozzle part | 2500 | 41 | 95 | 58 | 1.6 | ○ | low LD container and liquid surface distance |

As is clear from the results of Table 6, even when a container with the same aspect ratio L/D is used, when the immersion part is shallow and the aspect ratio Z/d is small, and when the distance from the outlet opening of the nozzle part to the liquid surface is large, preferable suspending property cannot be achieved. The results show that, under the conditions of the above-mentioned Experimental Example 4, preferable suspending property cannot be achieved when the aspect ratio Z/d of the immersion part is not more than 1.24, and preferable suspending property can be obtained when the aspect ratio Z/d exceeds 1.24.

Experimental Example 5: Test Relating to Suspending Property when Kind of Medium is Changed In Experimental Example 5, suspending property of a liquid medium composition produced by changing the kind of the medium as the second liquid was examined. The temperature of the second liquid contained in the container was maintained at 37° C., and the temperature of the first liquid was set to room temperature (RT).

The dispersed state (suspending action) of beads and the state of structure in each Experimental Example is shown in Table 7.

method) or the medium composition of Example 7 at 33333 cells/mL, and dispensed to the wells of a 96 well flat bottom ultra-low adhesive surface microplate (Corning Incorporated manufactured by, #3474) at 150 μL per 1 well. As a negative control, A549 cells were suspended in the above-mentioned medium free of deacylated gellan gum and dispensed. Successively, the plate was cultured in a static state in a $CO_2$ incubator (37° C., 5% $CO_2$) for 7 days. ATP reagent (150 μL, CellTiter-Glo™ Luminescent Cell Viability Assay, manufactured by Promega) was added to the culture medium on day 0 immediately after seeding and 7 days after culture and suspended therein, stood for about 10 min at room temperature, and the luminescence intensity (RLU value) was measured by FlexStation3 (manufactured by Molecular Devices), from which the luminescence with the medium alone was subtracted to measure the number of viable cells. The above experiment was performed 3 times.

A method using the medium composition by the production method of the present invention showed the same level of proliferation of A549 cells as compared to the conventional method. RLU values (ATP measurement, luminescence intensity) at culture day number 0 and 7 days later of static culture are shown in Table 8 as a mean of 3 tests.

TABLE 7

| test No | second liquid B | | | | first liquid A | | | evaluation results | |
|---|---|---|---|---|---|---|---|---|---|
| | kind | amount added [mL] | stirring [rpm] | temperature [° C.] | concentration [%] | amount added [mL] | temperature [° C.] | suspended state of beads | state of structure |
| c1 | RPMI | 30 | 0 | 37 | 0.8 | 0.8 | RT | ○ | ○ |
| c2 | DMEM | 40 | 0 | 37 | 0.8 | 0.8 | RT | ○ | ○ |
| c3 | DMEM-F12 | 40 | 0 | 37 | 0.8 | 0.8 | RT | ○ | ○ |
| c4 | Ham's F12 | 40 | 0 | 37 | 0.8 | 0.8 | RT | ○ | ○ |
| c5 | EMEM | 40 | 0 | 37 | 0.8 | 0.8 | RT | ○ | ○ |

As is clear from the results of Table 7, even when the second liquid is different, the first liquid and the second liquid can be mixed well, and preferable suspending property can be obtained.

Experimental Example 6: Cell Proliferation Experiment of A549 Cells Using Low Adhesion Plate Deacylated gellan gum (KELCOGEL CG-LA, manufactured by Sansho Co., Ltd.) was suspended in ultra pure water (Milli-Q water) to 0.3% (w/v) or 0.75% (w/v), dissolved by stirring with heating at 90° C., and this aqueous solution was autoclave sterilized at 121° C. for 20 min. Using 0.3% solution, a medium composition was prepared by adding deacylated gellan gum (final concentration 0.015% (w/v)) to DMEM medium (manufactured by WAKO) containing 10% (v/v) fetal bovine serum. Fetal bovine serum was added at 10% (v/v) to a medium composition prepared by a conventional method (method using homomixer as described in Example of JP-B-5629893) or Example 7.

Human lung cancer cell line A549 (manufactured by DS PHARMA BIOMEDICAL) was seeded in the above-mentioned medium composition containing fetal bovine serum and added with deacylated gellan gum (conventional

TABLE 8

| | culture day number | 0 | 7 |
|---|---|---|---|
| | negative control | 9361 | 29610 |
| conventional method | deacylated gellan gum | 7811 | 97182 |
| production method of present invention | deacylated gellan gum | 7500 | 95840 |

As is clear from the results of Table 8, the medium composition produced by the production method of the present invention was suggested to enable suspension culture of cells and promote cell proliferation, as with the medium composition produced by the conventional method.

Experimental Example 7: A549 Cell Proliferation Suppressive Test Using Trametinib and MK-2206 in Low Adhesion Plate Deacylated gellan gum (KELCOGEL CG-LA, manufactured by Sansho Co., Ltd.) was suspended in ultra pure water (Milli-Q water) to 0.3% (w/v) or 0.75% (w/v), dissolved by stirring with heating at 90° C., and this aqueous solution was autoclave sterilized at 121° C. for 20 min. Using 0.3% solution, a medium composition was prepared by adding deacylated gellan gum (final concentration 0.015% (w/v)) to DMEM medium (manufactured by WAKO) containing 10% (v/v) fetal bovine serum. Fetal bovine serum was added at 10% (v/v) to a medium composition prepared in Example 7.

Human lung cancer cell line A549 (manufactured by DS PHARMA BIOMEDICAL) was seeded in the above-mentioned medium composition added with deacylated gellan gum (conventional method) or the medium composition of Example 7 at 14800 cells/mL, and dispensed to the wells of a 96 well flat bottom ultra-low adhesive surface microplate (Corning Incorporated manufactured by, #3474) at 135 μL per 2 well. As a negative control, A549 cells were suspended in the above-mentioned medium free of deacylated gellan gum and dispensed. Each plate was cultured in a static state in a $CO_2$ incubator (37° C., 5% $CO_2$). On day 1 of culture, medium compositions (conventional method and the production method of the present invention) containing each anticancer agent at 10-fold concentration and deacylated gellan gum (final concentration 0.015% (w/v)), and a medium composition containing each anticancer agent alone at 10-fold concentration (non-addition method), 15 μL each, was added to a final concentration of 0.001 to 30 μM, and culture was continued for 7 days. As the anticancer agent, Trametinib (manufactured by Santa Cruz, MEK inhibitor) and MK-2206 (manufactured by Santa Cruz, Akt inhibitor) were used. ATP reagent (150 μL, CellTiter-Glo™ Luminescent Cell Viability Assay, manufactured by Promega) was added to the culture media on days 5 and 8 and suspended therein, stood for about 10 min at room temperature, and the luminescence intensity (RLU value) was measured by FlexStation3 (manufactured by Molecular Devices), from which the luminescence with the medium alone was subtracted to measure the number of viable cells.

The suppressive effect of each anticancer agent on A549 cell proliferation was not different and similar between the medium composition produced by the production method of the present invention and the medium composition produced by a conventional method, and it was found that the medium composition of the present invention also shows strong efficacy of MK-2206. In addition, % control of RLU value (ATP measurement, luminescence intensity) on day 4 of static culture is shown in Table 9, and % control of RLU value (ATP measurement, luminescence intensity) on day 7 of static culture is shown in Table 10.

TABLE 9

| culture conditions | | non-addition method | conventional method | production method of present invention |
|---|---|---|---|---|
| % Control | DMSO | 100 | 100 | 100 |
| | Paclitaxel 0.001 μM | 112 | 98 | 91 |
| | Paclitaxel 0.01 μM | 57 | 31 | 32 |
| | Trametinib 0.001 μM | 76 | 85 | 82 |
| | Trametinib 0.003 μM | 57 | 65 | 60 |
| | Trametinib 0.01 μM | 65 | 61 | 57 |
| | Trametinib 0.03 μM | 46 | 40 | 41 |
| | MK-2206 0.03 μM | 108 | 100 | 85 |
| | MK-2206 0.1 μM | 99 | 91 | 74 |
| | MK-2206 0.3 μM | 93 | 71 | 60 |
| | MK-2206 1 μM | 78 | 50 | 43 |
| | MK-2206 3 μM | 62 | 38 | 33 |

TABLE 10

| culture conditions | | non-addition method | conventional method | production method of present invention |
|---|---|---|---|---|
| % Control | DMSO | 100 | 100 | 100 |
| | Paclitaxel 0.001 μM | 116 | 90 | 84 |
| | Paclitaxel 0.01 μM | 49 | 12 | 12 |
| | Trametinib 0.001 μM | 76 | 81 | 76 |
| | Trametinib 0.003 μM | 48 | 52 | 48 |
| | Trametinib 0.01 μM | 56 | 48 | 45 |
| | Trametinib 0.03 μM | 39 | 25 | 24 |
| | MK-2206 0.03 μM | 124 | 92 | 80 |
| | MK-2206 0.1 μM | 101 | 83 | 69 |
| | MK-2206 0.3 μM | 103 | 63 | 54 |
| | MK-2206 1 μM | 85 | 38 | 34 |
| | MK-2206 3 μM | 76 | 26 | 21 |

As is clear from the results of Table 9, Table 10, the medium composition produced by the production method of the present invention was suggested to enable suspension culture of cells and potentiate a proliferation-suppressive effect of the anticancer agent against cancer cells, as with the medium composition produced by the conventional method.

Experimental Example 8: Comparison with Monolayer Culture Method in Proliferation Action on Panc02,03 Cell Stimulated by Each Growth Factor Deacylated gellan gum (KELCOGEL CG-LA, manufactured by Sansho Co., Ltd.) was suspended in ultra pure water (Milli-Q water) to 0.75% (w/v), dissolved by stirring with heating at 90° C., and this aqueous solution was autoclave sterilized at 121° C. for 20 min. In the same manner as in Example 7, a medium composition was produced by adding deacylated gellan gum (final concentration 0.02% (w/v)) to RPMI1640 medium (manufactured by WAKO) containing fetal bovine serum at 15% (v/v) and used as Example 13.

Human pancreatic cancer cell line Panc02,03 (manufactured by ATCC) was seeded at 37000 cells/mL in the medium composition of Example 13 (manufactured by the production method of the present invention), and dispensed to the wells of a 96 well flat bottom ultra-low adhesive surface microplate (Corning Incorporated manufactured by, #3474) at 135 μL per 1 well. As a negative control, Panc02, 03 cells were suspended in the above-mentioned medium free of deacylated gellan gum and dispensed. As a monolayer culture method, human pancreatic cancer cell line Panc02,03 cells were seeded at 2200 cells/mL in the above-mentioned medium composition free of deacylated gellan gum, and dispensed to the wells of a 96 well flat bottom microplate (manufactured by Corning Incorporated, #3585) at 135 μL per 1 well. Each plate was cultured in a static state in a $CO_2$ incubator (37° C., 5% $CO_2$). On day 1 of culture, medium compositions (manufactured by conventional method and the production method of the present invention) containing 10-fold concentration of human HB-EGF (manufactured by PEPROTECH) to a final concentration of 30, 100 ng/mL, 10-fold concentration of human EGF (manufactured by PEPROTECH) to 3, 30 ng/mL, 10-fold concentration of human FGF2 (manufactured by PEPROTECH) to 10, 100 ng/mL, 10-fold concentration of human TGF-β1 (manufactured by PEPROTECH) to 3, 30 ng/mL, 10-fold concentration of human PDGF-BB (manufactured by PEPROTECH) to 10 ng/mL or 10-fold concentration of human IGF-1 (manufactured by PEPROTECH) to 10, 100 ng/mL, and a final concentration 0.015% (w/v) of deacylated gellan gum, each 15 μL, were added. In a monolayer culture group and a negative control group, a medium composition containing a 10-fold concentration of each growth factor alone was added by 15 μL each. Culturing was continued for 5 days. ATP reagent (150 μL, CellTiter-Glo™ Luminescent Cell Viability Assay, manufactured by Promega) was added to the culture media on day 6 and suspended therein, stood for about 10 min at room temperature, and the luminescence intensity (RLU value) was measured by FlexStation3 (manufactured by Molecular Devices), from which the luminescence with the medium alone was subtracted to measure the number of viable cells.

As a result, it was found that the efficacy of human HB-EGF and human EGF is strongly shown by Panc02,03 cell proliferation test method using the medium composition by the production method of the present invention, as compared to a monolayer culture method and negative control group. In addition, % control of RLU value (ATP measurement, luminescence intensity) on day 6 of static culture is shown in Table 11.

TABLE 11

| culture conditions on day 8 | | monolayer culture group | negative control group | Example 13 |
|---|---|---|---|---|
| % Control | no addition | 100 | 100 | 100 |
| | human HB-EGF 30 ng/mL | 99 | 132 | 118 |
| | human HB-EGF 100 ng/mL | 98 | 134 | 202 |
| | human EGF 3 ng/mL | 105 | 117 | 108 |
| | human EGF 30 ng/mL | 97 | 136 | 187 |
| | human FGF-2 10 ng/mL | 108 | 118 | 107 |
| | human FGF-2 100 ng/mL | 102 | 99 | 100 |
| | human TGF-β1 3 ng/mL | 95 | 114 | 102 |
| | human TGF-β1 30 ng/mL | 99 | 122 | 106 |
| | human IGF-1 10 ng/mL | 101 | 119 | 100 |
| | human IGF-1 100 ng/mL | 98 | 121 | 110 |
| | human PDGF-BB 10 ng/mL | 98 | 128 | 101 |

As is clear from the results of Table 11, it was suggested that a medium composition produced by the production method of the present invention enables suspension culture of cells and promotes cell proliferation by HB-EGF or EGF stimulation, as with a medium composition produced by a conventional method.

INDUSTRIAL APPLICABILITY

According to the present invention, any liquid (particularly liquid medium) containing a linking substance such as divalent metal cation and the like can be easily mixed with a liquid containing a particular compound, and a liquid medium composition containing a fine structure dispersed therein can be produced.

This application is based on patent application No. 2015-078795 filed in Japan (filing date: Apr. 7, 2015), the contents of which are incorporated in full herein.

The invention claimed is:

1. A production method of a liquid medium composition, comprising steps of:
   passing a first liquid comprising a plurality of a particular compound of the following (i) through a through-hole having a cross-sectional area of 0.01 mm$^2$-5.00 mm$^2$ formed in a nozzle part at a flow rate of not less than 1.7 mL/sec, and
   injecting the first liquid into a second liquid comprising a linking substance of the following (ii) at said flow rate to form structures in which the particular compounds are bound via the linking substance and to disperse the structures in a mixture of the first and second liquids, wherein the first liquid and the second liquid in the mixture of the first and second liquids have a volume ratio (first liquid:second liquid) of from 1:5 to 1:500:
   (i) a particular compound which is a polymer compound having an anionic functional group, and capable of forming a structure by linking via a divalent metal cation, which structure being capable of suspending a cell or a tissue, wherein the polymer compound is composed of one or more of hyaluronic acid, gellan gum, deacylated gellan gum, rhamsan gum, diutan gum, xanthan gum, carageenan, hexuronic acid, fucoidan, pectin, pectic acid, pectinic acid, heparan sulfate, heparin, heparitin sulfate, keratosulfate, chondroitin sulfate, dermatan sulfate, rhamnan sulfate, and a salts thereof, and
   (ii) a linking substance which is a divalent metal cation, wherein the divalent metal cation is a calcium ion, a magnesium ion, or a combination thereof,
   wherein the liquid medium composition has a viscosity of not more than 8 mPa·s at 37° C.

2. The production method according to claim 1, wherein the second liquid is placed in a container of the following (a), and the first liquid is fed out from a supply device and passed through the through-hole of a container of the following (a) at the above-mentioned flow rate, whereby the first liquid is injected into the second liquid in the container at said flow rate:
   (a) a container comprising a body and a lid, said body or lid provided with a nozzle part having a through-hole communicating the outside of the container and the inside of the container, and said through-hole having a cross-sectional area of 0.01 mm$^2$-5.00 mm$^2$.

3. The production method according to claim 2, wherein the supply device is a syringe, the nozzle part is provided on the lid of the container, and a tubular component for fitting a syringe tip protrudes from an outer surface of the lid at a container external side of the nozzle part.

4. The production method according to claim 1, wherein the second liquid is placed in a container of the following (a), a tip of a nozzle part of a supply device of the following (b) containing the first liquid is inserted into the container, and the first liquid is fed out from the supply device and passed through the through-hole in the nozzle part of the supply device, whereby the first liquid is injected into the second liquid in the container at said flow rate:
   (a) a container comprising a body and a lid, and
   (b) a supply device comprising a container part for containing a liquid, and a nozzle part for injecting the contained liquid through a through-hole, said through-hole having a cross-sectional area of 0.01 mm$^2$-5.00 mm$^2$.

5. The production method according to claim 4, wherein the supply device is a syringe, the nozzle part is an injection needle mounted on the syringe, the lid of the container of (a) is provided with a penetrable part permitting penetration of a needle tube part of the injection needle from the outside of the container to the inside of the container, and a tubular component for fitting a needle base part of the injection needle protrudes from an outer surface of the lid at a container external side of the penetrable part.

6. The production method according to claim 1, wherein the polymer compound is deacylated gellan gum, and the first liquid is an aqueous solution containing deacylated gellan gum.

7. The production method according to claim 2, wherein the polymer compound is deacylated gellan gum, and the first liquid is an aqueous solution containing deacylated gellan gum.

8. The production method according to claim 3, wherein the polymer compound is deacylated gellan gum, and the first liquid is an aqueous solution containing deacylated gellan gum.

9. The production method according to claim 4, wherein the polymer compound is deacylated gellan gum, and the first liquid is an aqueous solution containing deacylated gellan gum.

10. The production method according to claim 5, wherein the polymer compound is deacylated gellan gum, and the first liquid is an aqueous solution containing deacylated gellan gum.

* * * * *